US009830426B2

(12) United States Patent
Arnold et al.

(10) Patent No.: US 9,830,426 B2
(45) Date of Patent: Nov. 28, 2017

(54) FITNESS MONITORING DEVICE WITH USER ENGAGEMENT METRIC FUNCTIONALITY

(71) Applicant: Fitbit, Inc., San Francisco, CA (US)

(72) Inventors: Jacob Antony Arnold, Fremont, CA (US); Jung Ook Hong, San Jose, CA (US); Shelten Gee Jao Yuen, Berkeley, CA (US)

(73) Assignee: Fitbit, Inc., San Francisco, CA (US)

( * ) Notice: Subject to any disclaimer, the term of this patent is extended or adjusted under 35 U.S.C. 154(b) by 0 days.

(21) Appl. No.: 14/887,075

(22) Filed: Oct. 19, 2015

(65) Prior Publication Data

US 2016/0042142 A1  Feb. 11, 2016

Related U.S. Application Data

(60) Division of application No. 14/497,177, filed on Sep. 25, 2014, now Pat. No. 9,202,111, which is a
(Continued)

(51) Int. Cl.
*G06F 19/00* (2011.01)
*G06K 9/00* (2006.01)
(Continued)

(52) U.S. Cl.
CPC .......... *G06F 19/3431* (2013.01); *A63B 71/06* (2013.01); *G01G 19/44* (2013.01);
(Continued)

(58) Field of Classification Search
CPC .................................................. G06F 19/3431
(Continued)

(56) References Cited

U.S. PATENT DOCUMENTS 1,924,652 A    8/1933  Rivas et al.
3,321,036 A    5/1967  Keenan et al.
(Continued)

FOREIGN PATENT DOCUMENTS

EP    1 721 237    8/2012
GB    2454705 A    5/2009
(Continued)

OTHER PUBLICATIONS

US Office Action, dated May 21, 2015, issued in U.S. Appl. No. 14/497,177.
(Continued)

*Primary Examiner* — Thomas Hong
(74) *Attorney, Agent, or Firm* — Weaver Austin Villeneuve & Sampson LLP

(57) ABSTRACT

Methods, apparatuses, and systems are provided for interacting with a user to promote engagement with a fitness monitoring device configured to measure a fitness parameter of the user, which may include determining, by one or more processors in at least one of the fitness monitoring device or a device in communication with the fitness monitoring device, that user engagements with the fitness monitoring device have occurred on multiple occasions, in which each user engagement produces at least one measurement of the fitness parameter; receiving, by the one or more processors, information indicating a level of engagement metric for the user based, at least in part, on multiple detected the multiple user engagements with the fitness monitoring device; and generating, by the one or more processors and based on the level of engagement metric, a notification containing information relating to at least a level of user engagement with the fitness monitoring device or the fitness parameter.

12 Claims, 12 Drawing Sheets

Related U.S. Application Data continuation-in-part of application No. 14/201,467, filed on Mar. 7, 2014, which is a continuation of application No. 14/027,164, filed on Sep. 14, 2013, now Pat. No. 8,747,312, which is a division of application No. 13/929,868, filed on Jun. 28, 2013, now Pat. No. 8,696,569, which is a division of application No. 13/346,275, filed on Jan. 9, 2012, now Pat. No. 8,475,367.

(60) Provisional application No. 61/898,326, filed on Oct. 31, 2013, provisional application No. 61/431,020, filed on Jan. 9, 2011.

(51) Int. Cl.
| | |
|---|---|
| *A63B 71/06* | (2006.01) |
| *G01G 19/44* | (2006.01) |
| *G01G 19/50* | (2006.01) |
| *G01G 23/37* | (2006.01) |
| *G06F 3/041* | (2006.01) |
| *G06F 21/32* | (2013.01) |
| *G06Q 50/22* | (2012.01) |
| *G09B 5/00* | (2006.01) |
| *G09B 19/00* | (2006.01) |
| *G06Q 10/06* | (2012.01) |
| *G06Q 30/02* | (2012.01) |

(52) U.S. Cl.
CPC ......... *G01G 19/50* (2013.01); *G01G 23/3728* (2013.01); *G06F 3/0412* (2013.01); *G06F 19/3406* (2013.01); *G06F 19/3418* (2013.01); *G06F 19/3475* (2013.01); *G06F 19/3481* (2013.01); *G06F 21/32* (2013.01); *G06K 9/00342* (2013.01); *G06Q 10/0639* (2013.01); *G06Q 30/0207* (2013.01); *G06Q 50/22* (2013.01); *G09B 5/00* (2013.01); *G09B 19/0038* (2013.01); *G09B 19/0092* (2013.01); *A63B 2220/803* (2013.01); *A63B 2225/50* (2013.01); *A63B 2230/75* (2013.01); *Y10S 128/92* (2013.01)

(58) Field of Classification Search
USPC .......................................................... 434/236
See application file for complete search history.

(56) References Cited

U.S. PATENT DOCUMENTS

| | | | |
|---|---|---|---|
| 4,301,879 | A | 11/1981 | Dubow |
| 4,312,358 | A | 1/1982 | Barney |
| 4,318,447 | A | 3/1982 | Northcutt |
| 4,366,873 | A | 1/1983 | Levy et al. |
| 4,367,752 | A | 1/1983 | Jimenez et al. |
| 4,423,792 | A | 1/1984 | Cowan |
| 4,433,741 | A | 2/1984 | Ryckman, Jr. |
| 4,576,244 | A | 3/1986 | Zeigner et al. |
| 4,577,710 | A | 3/1986 | Ruzumna |
| 4,578,769 | A | 3/1986 | Frederick |
| 4,605,080 | A | 8/1986 | Lemelson |
| 4,757,453 | A | 7/1988 | Nasiff |
| 4,773,492 | A | 9/1988 | Ruzumna |
| 4,977,509 | A | 12/1990 | Pitchford et al. |
| 5,058,427 | A | 10/1991 | Brandt |
| 5,224,059 | A | 6/1993 | Nitta et al. |
| 5,295,085 | A | 3/1994 | Hoffacker |
| 5,323,650 | A | 6/1994 | Fullen et al. |
| 5,415,176 | A | 5/1995 | Sato et al. |
| 5,583,776 | A | 12/1996 | Levi et al. |
| 5,611,351 | A | 3/1997 | Sato et al. |
| 5,620,003 | A | 4/1997 | Sepponen |
| 5,664,270 | A | 9/1997 | Bell |
| 5,671,162 | A | 9/1997 | Werbin |
| 5,724,265 | A | 3/1998 | Hutchings |
| 5,724,267 | A | 3/1998 | Richards |
| 5,832,417 | A | 11/1998 | Petrucelli et al. |
| 5,886,302 | A | 3/1999 | Germanton et al. |
| 5,891,042 | A | 4/1999 | Sham et al. |
| 5,899,963 | A | 5/1999 | Hutchings |
| 5,947,868 | A | 9/1999 | Dugan |
| 5,955,667 | A | 9/1999 | Fyfe |
| 5,976,083 | A | 11/1999 | Richardson et al. |
| 6,018,705 | A | 1/2000 | Gaudet et al. |
| 6,038,465 | A | 3/2000 | Melton, Jr. |
| 6,039,688 | A | 3/2000 | Douglas et al. |
| 6,145,389 | A | 11/2000 | Ebeling et al. |
| 6,183,425 | B1 | 2/2001 | Whalen et al. |
| 6,287,262 | B1 | 9/2001 | Amano et al. |
| 6,292,690 | B1 | 9/2001 | Petrucelli et al. |
| 6,301,964 | B1 | 10/2001 | Fyfe et al. |
| 6,305,221 | B1 | 10/2001 | Hutchings |
| 6,309,360 | B1 | 10/2001 | Mault |
| 6,369,337 | B1 | 4/2002 | Machiyama et al. |
| 6,370,425 | B1 | 4/2002 | Oguma |
| D460,010 | S | 7/2002 | Robinson |
| 6,471,087 | B1 | 10/2002 | Shusterman |
| 6,473,641 | B1 | 10/2002 | Kodama et al. |
| 6,473,643 | B2 | 10/2002 | Chai et al. |
| 6,477,409 | B2 | 11/2002 | Sakata et al. |
| 6,478,736 | B1 | 11/2002 | Mault |
| 6,480,736 | B1 | 11/2002 | Kodama et al. |
| 6,487,445 | B1 | 11/2002 | Serita et al. |
| RE37,954 | E | 1/2003 | Sato et al. |
| 6,513,381 | B2 | 2/2003 | Fyfe et al. |
| 6,513,532 | B2 | 2/2003 | Mault et al. |
| 6,529,827 | B1 | 3/2003 | Beason et al. |
| 6,532,385 | B2 | 3/2003 | Serizawa et al. |
| 6,538,215 | B2 | 3/2003 | Montagnino et al. |
| 6,552,553 | B2 | 4/2003 | Shoji et al. |
| 6,571,200 | B1 | 5/2003 | Mault |
| 6,583,369 | B2 | 6/2003 | Montagnino et al. |
| 6,612,984 | B1 | 9/2003 | Kerr, II |
| 6,621,013 | B2 | 9/2003 | Tanida et al. |
| 6,635,015 | B2 | 10/2003 | Sagel |
| 6,678,629 | B2 | 1/2004 | Tsuji |
| 6,752,760 | B2 | 6/2004 | Kouou |
| 6,761,064 | B2 | 7/2004 | Tsuji |
| 6,790,178 | B1 | 9/2004 | Mault et al. |
| 6,813,582 | B2 | 11/2004 | Levi et al. |
| 6,856,259 | B1 | 2/2005 | Sharp |
| 6,864,436 | B1 | 3/2005 | Nobes et al. |
| 6,956,175 | B1 | 10/2005 | Daly et al. |
| 6,963,035 | B2 | 11/2005 | Honda et al. |
| 6,975,961 | B1 | 12/2005 | Hong |
| 7,008,350 | B1 | 3/2006 | Yamazaki et al. |
| 7,062,225 | B2 | 6/2006 | White |
| 7,123,243 | B2 | 10/2006 | Kawasaki et al. |
| 7,162,368 | B2 | 1/2007 | Levi et al. |
| 7,171,331 | B2 | 1/2007 | Vock et al. |
| 7,195,600 | B2 | 3/2007 | Ueda et al. |
| 7,200,517 | B2 | 4/2007 | Darley et al. |
| 7,261,690 | B2 | 8/2007 | Teller et al. |
| 7,283,870 | B2 | 10/2007 | Kaiser et al. |
| 7,292,227 | B2 | 11/2007 | Fukumoto et al. |
| 7,304,252 | B1 | 12/2007 | Hunt et al. |
| 7,357,776 | B2 | 4/2008 | Nishibayashi et al. |
| 7,373,820 | B1 | 5/2008 | James |
| 7,457,724 | B2 | 11/2008 | Vock et al. |
| 7,479,949 | B2 | 1/2009 | Jobs et al. |
| 7,505,865 | B2 | 3/2009 | Ohkubo et al. |
| 7,523,040 | B2 | 4/2009 | Kirchhoff et al. |
| 7,547,851 | B1 | 6/2009 | Wong |
| 7,690,556 | B1 | 4/2010 | Kahn et al. |
| 7,691,068 | B2 | 4/2010 | Felder et al. |
| 7,720,855 | B2 | 5/2010 | Brown |
| 7,774,156 | B2 | 8/2010 | Niva et al. |
| 7,789,802 | B2 | 9/2010 | Lee et al. |
| 7,831,408 | B2 | 11/2010 | Petrucelli |
| 7,865,140 | B2 | 1/2011 | Levien et al. |
| 7,872,201 | B1 | 1/2011 | Whitney |
| 7,907,901 | B1 | 3/2011 | Kahn et al. |

(56) References Cited

U.S. PATENT DOCUMENTS

| | | | |
|---|---|---|---|
| 7,925,022 B2 | 4/2011 | Jung et al. |
| 7,927,253 B2 | 4/2011 | Vincent et al. |
| 7,941,665 B2 | 5/2011 | Berkema et al. |
| 7,967,731 B2 | 6/2011 | Kil |
| 7,983,876 B2 | 7/2011 | Vock et al. |
| 7,994,439 B2 | 8/2011 | Daniels et al. |
| 8,015,030 B2 | 9/2011 | Brown |
| 8,028,443 B2 | 10/2011 | Case, Jr. |
| 8,055,469 B2 | 11/2011 | Kulach et al. |
| 8,059,573 B2 | 11/2011 | Julian et al. |
| 8,081,168 B2 | 12/2011 | Mamba et al. |
| 8,095,071 B2 | 1/2012 | Sim et al. |
| 8,103,247 B2 | 1/2012 | Ananthanarayanan et al. |
| 8,157,730 B2 | 4/2012 | LeBoeuf et al. |
| 8,180,591 B2 | 5/2012 | Yuen et al. |
| 8,190,651 B2 | 5/2012 | Treu et al. |
| 8,213,613 B2 | 7/2012 | Diehl et al. |
| 8,260,261 B2 | 9/2012 | Teague |
| 8,265,901 B2 | 9/2012 | Petrucelli |
| 8,271,662 B1 | 9/2012 | Gossweiler, III et al. |
| 8,289,162 B2 | 10/2012 | Mooring et al. |
| 8,360,936 B2 | 1/2013 | DiBenedetto et al. |
| 8,457,732 B2 | 6/2013 | Fukada |
| 8,463,577 B2 | 6/2013 | Yuen et al. |
| 8,475,367 B1 | 7/2013 | Yuen et al. |
| 8,540,641 B2 | 9/2013 | Kroll et al. |
| 8,566,120 B2 | 10/2013 | Takehara |
| 8,639,226 B2 | 1/2014 | Hutchings et al. |
| 8,653,965 B1 | 2/2014 | Otto et al. |
| 8,696,569 B2 | 4/2014 | Yuen et al. |
| 8,719,202 B1 | 5/2014 | Maeng |
| 8,747,312 B2 | 6/2014 | Yuen et al. |
| 8,797,281 B2 | 8/2014 | Simmons |
| 9,084,536 B2 | 7/2015 | Yuen et al. |
| 9,084,537 B2 | 7/2015 | Yuen et al. |
| 9,084,538 B2 | 7/2015 | Yuen et al. |
| 9,173,576 B2 | 11/2015 | Yuen et al. |
| 9,173,577 B2 | 11/2015 | Yuen et al. |
| 9,202,111 B2 | 12/2015 | Arnold et al. |
| 9,247,884 B2 | 2/2016 | Yuen et al. |
| 9,433,357 B2 | 9/2016 | Yuen et al. |
| 2001/0056229 A1 | 12/2001 | Cosentino et al. |
| 2002/0022773 A1 | 2/2002 | Drinan et al. |
| 2002/0027164 A1 | 3/2002 | Mault et al. |
| 2002/0055857 A1 | 5/2002 | Mault |
| 2002/0087102 A1 | 7/2002 | Honda et al. |
| 2002/0107433 A1 | 8/2002 | Mault |
| 2002/0134589 A1 | 9/2002 | Montagnino et al. |
| 2002/0179338 A1 | 12/2002 | Tanida et al. |
| 2002/0183051 A1 | 12/2002 | Poor et al. |
| 2002/0188205 A1 | 12/2002 | Mills |
| 2002/0198740 A1 | 12/2002 | Roman et al. |
| 2003/0065257 A1 | 4/2003 | Mault et al. |
| 2003/0218532 A1 | 11/2003 | Hussmann |
| 2004/0016437 A1 | 1/2004 | Cobb et al. |
| 2004/0129463 A1 | 7/2004 | Carlucci et al. |
| 2004/0193069 A1 | 9/2004 | Takehara |
| 2004/0238228 A1 | 12/2004 | Montague et al. |
| 2005/0006152 A1 | 1/2005 | Eldeiry |
| 2005/0054938 A1 | 3/2005 | Wehman et al. |
| 2005/0059902 A1 | 3/2005 | Itagaki |
| 2005/0071197 A1 | 3/2005 | Goldberg |
| 2005/0107723 A1 | 5/2005 | Wehman et al. |
| 2005/0113650 A1 | 5/2005 | Pacione et al. |
| 2005/0176463 A1 | 8/2005 | Hollemans et al. |
| 2005/0177060 A1 | 8/2005 | Yamazaki et al. |
| 2005/0181386 A1 | 8/2005 | Diamond et al. |
| 2005/0228244 A1 | 10/2005 | Banet |
| 2005/0245794 A1 | 11/2005 | Thompson et al. |
| 2005/0247494 A1 | 11/2005 | Montagnino |
| 2005/0283051 A1 | 12/2005 | Chen |
| 2006/0020177 A1 | 1/2006 | Seo et al. |
| 2006/0047208 A1 | 3/2006 | Yoon |
| 2006/0116589 A1 | 6/2006 | Park |
| 2006/0122470 A1 | 6/2006 | Schulz |
| 2006/0143645 A1 | 6/2006 | Vock et al. |
| 2006/0173579 A1 | 8/2006 | Desrochers et al. |
| 2006/0205564 A1 | 9/2006 | Peterson |
| 2006/0217630 A1 | 9/2006 | Ueda et al. |
| 2006/0241360 A1 | 10/2006 | Montagnino et al. |
| 2006/0247606 A1 | 11/2006 | Batch |
| 2006/0259323 A1* | 11/2006 | Chan .................. G06Q 50/22 705/2 |
| 2006/0282006 A1 | 12/2006 | Petrucelli |
| 2007/0010721 A1 | 1/2007 | Chen et al. |
| 2007/0027401 A1 | 2/2007 | Shimomura et al. |
| 2007/0033069 A1 | 2/2007 | Rao et al. |
| 2007/0050715 A1 | 3/2007 | Behar |
| 2007/0051369 A1 | 3/2007 | Choi et al. |
| 2007/0073178 A1 | 3/2007 | Browning et al. |
| 2007/0142179 A1 | 6/2007 | Terao et al. |
| 2007/0142715 A1 | 6/2007 | Banet et al. |
| 2007/0167286 A1 | 7/2007 | Roes |
| 2007/0236475 A1 | 10/2007 | Wherry |
| 2007/0238938 A1 | 10/2007 | Nishibayashi et al. |
| 2007/0244739 A1 | 10/2007 | Soito et al. |
| 2008/0039140 A1 | 2/2008 | Morris et al. |
| 2008/0077436 A1 | 3/2008 | Muradia |
| 2008/0140338 A1 | 6/2008 | No et al. |
| 2008/0146277 A1 | 6/2008 | Anglin et al. |
| 2008/0146961 A1 | 6/2008 | Okura et al. |
| 2008/0154645 A1 | 6/2008 | Takehara |
| 2008/0155077 A1 | 6/2008 | James |
| 2008/0174570 A1 | 7/2008 | Jobs et al. |
| 2008/0183398 A1 | 7/2008 | Petrucelli |
| 2008/0203144 A1 | 8/2008 | Kim |
| 2008/0208479 A1 | 8/2008 | Roes |
| 2008/0221404 A1 | 9/2008 | Tso |
| 2008/0306767 A1 | 12/2008 | Bodlaender et al. |
| 2008/0314973 A1 | 12/2008 | Zuhars et al. |
| 2009/0018797 A1 | 1/2009 | Kasama et al. |
| 2009/0024053 A1 | 1/2009 | Kasahara |
| 2009/0041306 A1 | 2/2009 | Kwong |
| 2009/0043531 A1 | 2/2009 | Kahn et al. |
| 2009/0048044 A1 | 2/2009 | Oleson et al. |
| 2009/0089672 A1 | 4/2009 | Tseng et al. |
| 2009/0105047 A1 | 4/2009 | Guidi et al. |
| 2009/0118589 A1 | 5/2009 | Ueshima et al. |
| 2009/0204422 A1 | 8/2009 | James et al. |
| 2009/0240113 A1 | 9/2009 | Heckerman |
| 2010/0004977 A1* | 1/2010 | Marci .................. G06Q 10/10 705/7.32 |
| 2010/0007460 A1 | 1/2010 | Hayashi et al. |
| 2010/0009810 A1 | 1/2010 | Trzecieski |
| 2010/0043056 A1 | 2/2010 | Ganapathy |
| 2010/0049471 A1* | 2/2010 | Gage .................. G06F 19/3475 702/173 |
| 2010/0079291 A1 | 4/2010 | Kroll et al. |
| 2010/0130831 A1 | 5/2010 | Sato et al. |
| 2010/0227302 A1 | 9/2010 | McGilvery et al. |
| 2010/0275033 A1 | 10/2010 | Gillespie et al. |
| 2010/0331145 A1 | 12/2010 | Lakovic et al. |
| 2010/0331629 A1 | 12/2010 | Sato et al. |
| 2011/0003665 A1 | 1/2011 | Burton et al. |
| 2011/0022349 A1 | 1/2011 | Stirling et al. |
| 2011/0032105 A1 | 2/2011 | Hoffman et al. |
| 2011/0050394 A1 | 3/2011 | Zhang et al. |
| 2011/0068931 A1 | 3/2011 | Abernethy et al. |
| 2011/0087137 A1 | 4/2011 | Hanoun |
| 2011/0087438 A1 | 4/2011 | Maeir et al. |
| 2011/0106449 A1 | 5/2011 | Chowdhary et al. |
| 2011/0109540 A1 | 5/2011 | Milne et al. |
| 2011/0131005 A1 | 6/2011 | Ueshima et al. |
| 2011/0143322 A1 | 6/2011 | Tsang |
| 2011/0165998 A1 | 7/2011 | Lau et al. |
| 2011/0166628 A1 | 7/2011 | Jain |
| 2011/0184247 A1 | 7/2011 | Contant et al. |
| 2011/0191158 A1 | 8/2011 | Kateraas et al. |
| 2011/0196617 A1 | 8/2011 | Petrucelli |
| 2011/0197157 A1 | 8/2011 | Hoffman et al. |
| 2012/0033807 A1 | 2/2012 | Asim et al. |
| 2012/0059911 A1 | 3/2012 | Randhawa et al. |
| 2012/0072165 A1 | 3/2012 | Jallon |
| 2012/0083715 A1 | 4/2012 | Yuen et al. |

(56) References Cited

U.S. PATENT DOCUMENTS

| | | |
|---|---|---|
| 2012/0109676 A1 | 5/2012 | Landau |
| 2012/0150074 A1 | 6/2012 | Yanev et al. |
| 2012/0150483 A1 | 6/2012 | Vock et al. |
| 2012/0221634 A1 | 8/2012 | Treu et al. |
| 2012/0226111 A1 | 9/2012 | LeBoeuf et al. |
| 2012/0239173 A1 | 9/2012 | Laikari et al. |
| 2012/0254987 A1 | 10/2012 | Ge et al. |
| 2012/0274508 A1 | 11/2012 | Brown et al. |
| 2012/0297229 A1 | 11/2012 | Desai et al. |
| 2012/0297440 A1 | 11/2012 | Reams et al. |
| 2013/0106684 A1 | 5/2013 | Weast et al. |
| 2013/0289889 A1 | 10/2013 | Yuen et al. |
| 2014/0012512 A1 | 1/2014 | Yuen et al. |
| 2014/0018706 A1 | 1/2014 | Yuen et al. |
| 2014/0073486 A1* | 3/2014 | Ahmed .............. A61B 5/02405 482/9 |
| 2014/0095208 A1 | 4/2014 | Goldberg |
| 2014/0099614 A1 | 4/2014 | Hu et al. |
| 2014/0182952 A1 | 7/2014 | Yuen et al. |
| 2014/0257053 A1 | 9/2014 | Yuen et al. |
| 2014/0257709 A1 | 9/2014 | Yuen et al. |
| 2014/0326517 A1* | 11/2014 | Gomez .................. G01G 19/50 177/1 |
| 2014/0343443 A1 | 11/2014 | Yuen et al. |
| 2014/0371887 A1 | 12/2014 | Hoffman et al. |
| 2014/0377729 A1 | 12/2014 | Yuen et al. |
| 2014/0379275 A1 | 12/2014 | Yuen et al. |
| 2015/0011845 A1 | 1/2015 | Yuen et al. |
| 2015/0018991 A1 | 1/2015 | Arnold et al. |
| 2016/0349104 A1 | 12/2016 | Yuen et al. |

FOREIGN PATENT DOCUMENTS

| | | |
|---|---|---|
| JP | 11-347021 | 12/1999 |
| WO | WO 02/28123 A1 | 4/2002 |
| WO | WO 02/084568 A1 | 10/2002 |
| WO | WO 2007/102708 A1 | 9/2007 |
| WO | WO 2010/001318 A1 | 1/2010 |

OTHER PUBLICATIONS

US Notice of Allowance, dated Sep. 3, 2015, issued in U.S. Appl. No. 14/497,177.
US Office Action, dated Sep. 26, 2012, issued in U.S. Appl. No. 13/346,275.
US Final Office Action, dated Feb. 4, 2013, issued in U.S. Appl. No. 13/346,275.
US Notice of Allowance, dated Mar. 7, 2013, issued in U.S. Appl. No. 13/346,275.
US Office Action, dated Oct. 9, 2013, issued in U.S. Appl. No. 13/929,868.
US Notice of Allowance, dated Feb. 5, 2014, issued in U.S. Appl. No. 13/929,868.
US Office Action, dated Dec. 3, 2013, issued in U.S. Appl. No. 14/027,164.
US Notice of Allowance, dated Apr. 9, 2014, issued in U.S. Appl. No. 14/027,164.
US Office Action, dated Oct. 16, 2014, issued in U.S. Appl. No. 14/201,467.
US Final Office Action, dated Feb. 10, 2015, issued in U.S. Appl. No. 14/201,467.
US Office Action, dated Jul. 14, 2015, issued in U.S. Appl. No. 14/201,467.
US Office Action, dated Mar. 5, 2015, issued in U.S. Appl. No. 14/493,156.
US Final Office Action, dated Jul. 14, 2015, issued in U.S. Appl. No. 14/493,156.
US Notice of Allowance, dated Sep. 25, 2015, issued in U.S. Appl. No. 14/493,156.
US Office Action, dated Sep. 25, 2014, issued in U.S. Appl. No. 14/201,478.
US Final Office Action, dated Feb. 11, 2015, issued in U.S. Appl. No. 14/201,478.
US Notice of Allowance, dated May 6, 2015, issued in U.S. Appl. No. 14/201,478.
US Office Action, dated Dec. 19, 2014, issued in U.S. Appl. No. 14/476,128.
US Notice of Allowance, dated May 7, 2015, issued in U.S. Appl. No. 14/476,128.
US Office Action, dated Sep. 25, 2014, issued in U.S. Appl. No. 14/261,354.
US Final Office Action, dated Feb. 11, 2015, issued in U.S. Appl. No. 14/261,354.
US Final Office Action, dated Apr. 9, 2015, issued in U.S. Appl. No. 14/261,354.
US Notice of Allowance, dated Jul. 10, 2015, issued in U.S. Appl. No. 14/261,354.
US Office Action, dated Dec. 17, 2014, issued in U.S. Appl. No. 14/476,143.
US Final Office Action, dated Apr. 8, 2015, issued in U.S. Appl. No. 14/476,143.
US Notice of Allowance, dated Jul. 10, 2015, issued in U.S. Appl. No. 14/476,143.
US Office Action, dated Dec. 3, 2014, issued in U.S. Appl. No. 14/448,965.
US Notice of Allowance, dated Apr. 15, 2015, issued in U.S. Appl. No. 14/448,965.
US Office Action, dated Dec. 18, 2013, issued in U.S. Appl. No. 14/027,166.
US Final Office Action, dated Apr. 30, 2014, issued in U.S. Appl. No. 14/027,166.
US Office Action, dated Feb. 24, 2015, issued in U.S. Appl. No. 14/027,166.
"Activator is One of the Best Cydia iPhone Hacks | Control your iPhone with Gestures," Iphone-tips-and-advice.com, [retrieved on Jul. 9, 2013 at http://www.iphone-tips-and-advice.com/activatior.html], 10 pp.
Antoniou, Z, et al., (2007) "Intuitive mobile user interaction in smart spaces via NFC-enhanced devices," *Proceedings of the Third International Conference on Wireless and Mobile Communications* (ICWMC'07), pp. 1-6.
Chudnow, Alan (Dec. 3, 2012) "Basis Wristband Make Its Debut," *The Wired Self, Living in a Wired World*, published in Health [retrieved on Jul. 22, 2013 at http://thewiredself.com/health/basis-wrist-band-make-its-debut/], 3pp.
Clifford et al., (Nov. 2006) "Altimeter and Barometer System," *Freescale Semiconductor* Application Note AN1979, Rev 3, pp. 1-10.
DesMarais, Christina (posted on Sep. 3, 2013) "Which New Activity Tracker is Best for You?" *Health and Home, Health & Fitness, Guides & Reviews*, [Retrieved on Sep. 23, 2013 at http://www.techlicious.com/guide/which-new-activity-tracker-is-right-for-you/] 4 pp.
Empson, Rip, (Sep. 22, 2011) "Basis Reveals an Awesome New Affordable Heart and Health Tracker You Can Wear on Your Wrist," [retrieved on Sep. 23, 2013 at http://techcrunch.com/2011/09/22/basis-reveals-an-awesome-new . . . ], 3 pp.
Fang et al., (Dec. 2005) "Design of a Wireless Assisted Pedestrian Dead Reckoning System—The NavMote Experience," *IEEE Transactions on Instrumentation and Measurement*, 54(6):2342-2358.
Fitbit User's Manual, Last Updated Oct. 22, 2009, 15 pages.
Forerunner® 201 personal trainer owner's manual, (Feb. 2006) Garmin Ltd., 48 pp.
Forerunner® 301 personal trainer owner's manual, (Feb. 2006) Garmin Ltd., 66 pp.
Forerunner® 50 with ANT+Sport™ wireless technology, Owner's Manual, (Nov. 2007) Garmin Ltd., 44 pp.
Forerunner® 205/305 Owner's Manual, GPS-enabled trainer for runners, (2006-2008), Garmin Ltd., 80 pp.
Forerunner® 405CX Owner's Manual, "GPS-Enabled Sports Watch With Wireless Sync," (Mar. 2009), Garmin Ltd., 56 pp.
Forerunner® 110 Owner's Manual, (2010) "GPS-Enabled Sport Watch," Garmin Ltd., 16 pp.

(56) References Cited

OTHER PUBLICATIONS

Forerunner® 210 Owner's Manual, (2010) "GPS-Enabled Sport Watch," Garmin Ltd., 28 pp.
Forerunner® 410 Owner's Manual, (Jul. 2012) "GPS-Enabled Sport Watch With Wireless Sync," Garmin Ltd., 52 pp.
Forerunner® 10 Owner's Manual (Aug. 2012), Garmin Ltd., 10 pp.
Forerunner® 310XT Owner's Manual, Multisport GPS Training Device, (2009-2013), Garmin Ltd., 56 pp.
Forerunner® 405 Owner's Manual, (Mar. 2011) "GPS-Enabled Sport Watch With Wireless Sync," Garmin Ltd., 56 pp.
Forerunner® 910XT Owner's Manual, (Jan. 2013) Garmin Ltd., 56 pp.
Garmin Swim™ Owner's Manual (Jun. 2012), 12 pp.
Godfrey et al., (2008) "Direct measurement of human movement by accelerometry," *Medical Engineering & Physics*, 30:1364-1386.
Godha et al., (May 2008) "Foot mounted inertial system for pedestrian navigation," *Measurement Science and Technology*, 19(7):1-9.
Gonzalez-Landaeta et al. (Jul. 2008) "Heart rate detection from an electronic weighing scale," *Physiological Measurement*, 29(8):979.
Inan et al., (Mar 2010) "Adaptive cancellation of Floor vibrations in standing ballistocardiogram measurements using a seismic sensor as a noise reference," *IEEE Trans. on Biomedical Engineering*, 57(3):722-727.
Ladetto et al., (Sep. 2000) "On Foot Navigation: When GPS alone is not enough," *Journal of Navigation*, 53(2):279-285.
Lammel et al., (Sep. 2009) "Indoor Navigation with MEMS sensors," *Proceedings of the Eurosensors XXIII conference*, 1(1):532-535.
Larklife, User Manual, (2012) *Lark Technologies*, 7 pp.
Lark/Larkpro, User Manual, (2012) "What's in the box," *Lark Technologies*, 7 pp.
Lester et al., (2005) "A Hybrid Discriminative/Generative Approach for Modeling Human Activities," *Proc. of the Int'l Joint Conf. Artificial Intelligence*, pp. 766-772.
Lester et al., (2009) "Validated caloric expenditure estimation using a single body-worn sensor," *Proc. of the Int'l Conf. on Ubiquitous Computing*, pp. 225-234.
Linde et al., (2005) "Self-Weighing in Weight Gain Prevention and Weight Loss Trials," *Annals of Behavioral Medicine*, 30(3):210-216.
Nike+ FuelBand GPS Manual, User's Guide (Product Release Date Unknown, downloaded Jul. 22, 2013), 26 pages.
Nike+SportBand User's Guide, (Product Release Date Unknown, downloaded Jul. 22, 2013), 36 pages.
Nike+SportWatch GPS Manual, User's Guide, Powered by TOMTOM, (Product Release Date Unknown, downloaded Jul. 22, 2013), 42 pages.
Ohtaki et al. (Aug. 2005) "Automatic classification of ambulatory movements and evaluation of energy consumptions utilizing accelerometers and a barometer," *Microsystem Technologies*, 1(8-10):1034-1040.
Pärkkä et al., (Jan. 2006) "Activity Classification Using Realistic Data From Wearable Sensors," *IEEE Transactions on Information Technology in Biomedicine*, 10(1):119-128.
Pärkkä, J. et al., (2000) "A wireless wellness monitor for personal weight management," *IEEE*, pp. 83-88.
"Parts of Your Band," (Product Release Date Unknown, downloaded Jul. 22, 2013) Jawbone UP Band, 1 page.
Perrin et al., (2000) "Improvement of walking speed prediction by accelerometry and altimetry, validated by satellite positioning," Perrin, et al, *Medical & Biological Engineering & Computing*, 38:164-168.
Polar WearLink® + Coded Transmitter 31 Coded Transmitter W.I.N.D. User Manual, Polar® Listen to Your Body, *Manufactured by Polar Electro Oy*, 11 pages.
Rainmaker, (Jun. 25, 2012, updated Feb 16, 2013) "Garmin Swim watch In-Depth Review," [retrieved on Sep. 9, 2013 at http://www.derainmaker.com/2012/06/garmin-swim-in-depth-review.html, 38 pp.
Retscher (2006) "An Intelligent Multi-sensor System for Pedestrian Navigation," *Journal of Global Positioning Systems*, 5(1):110-118.
Sagawa et al. (Aug.-Sep. 1998) "Classification of Human Moving Patterns Using Air Pressure and Acceleration," *Proceedings of the 24th Annual Conference of the IEEE Industrial Electronics Society*, 2:1214-1219.
Sagawa et al. (Oct. 2000) "Non-restricted measurement of walking distance," *IEEE Int'l Conf. on Systems, Man, and Cybernetics*, 3:1847-1852.
"SCP1000-D01/D11 Pressure Sensor as Barometer and Altimeter," *VTI Technologies*, Jun. 2006, Application Note 33, 3 pages.
Stirling et al., (2005) "Evaluation of a New Method of Heading Estimation for Pedestrian Dead Reckoning Using Shoe Mounted Sensors," *Journal of Navigation*, 58:31-45.
"Suunto Lumi User Guide," *Suunto Oy*, Jun. and Sep. 1997, 49 pages.
Tanigawa et al., (Mar. 2008) "Drift-free dynamic height sensor using MEMS IMU aided by MEMS pressure sensor," *Workshop on Positioning, Navigation and Communication*, pp. 191-196.
"Tanita Ironman InnerScan body Composition Monitor," *Tanita Corporation*, Model MC-554 Manual, 2005.
"Using MS5534 for altimeters and barometers," *Intersema App., Note AN501*, Jan. 2006, 12 pp.
US Final Office Action, dated Nov. 5, 2015, issued in U.S. Appl. No. 14/201,467.
US Advisory Action, dated Feb. 10, 2016, issued in U.S. Appl. No. 14/201,467.
U.S. Appl. No. 15/220,275, filed Jul. 26, 2016, Yuen et al.
US Notice of Allowance, dated Apr. 26, 2016, issued in U.S. Appl. No. 14/201,467.

\* cited by examiner

FITNESS MONITORING DEVICE WITH USER ENGAGEMENT METRIC FUNCTIONALITY

CROSS REFERENCE TO RELATED APPLICATIONS

This application is a divisional of, and claims priority to, U.S. patent application Ser. No. 14/497,177, filed Sep. 25, 2014, which claims priority benefit under 35 U.S.C. §119(e) to U.S. Provisional Patent Application No. 61/898,326, filed Oct. 31, 2013, and titled "FITNESS MONITORING DEVICE WITH USER ENGAGEMENT METRIC FUNCTIONALITY," and which also claims priority as a continuation-in-part under 35 U.S.C. §120 to U.S. application Ser. No. 14/201,467, filed Mar. 7, 2014, and titled "BIOMETRIC MONITORING DEVICE HAVING A BODY WEIGHT SENSOR, AND METHODS OF OPERATING SAME," which is itself a continuation of U.S. patent application Ser. No. 14/027,164, filed Sep. 14, 2013, and now issued as U.S. Pat. No. 8,747,312 and titled "BIOMETRIC MONITORING DEVICE HAVING A BODY WEIGHT SENSOR, AND METHODS OF OPERATING SAME," which is itself a divisional of U.S. patent application Ser. No. 13/929,868, filed Jun. 28, 2013, and now issued as U.S. Pat. No. 8,696,569 and titled "BIOMETRIC MONITORING DEVICE HAVING A BODY WEIGHT SENSOR, AND METHODS OF OPERATING SAME," which is itself a divisional of U.S. patent application Ser. No. 13/346,275, filed Jan. 9, 2012, and now issued as U.S. Pat. No. 8,475,367, which itself claims benefit under 35 U.S.C. §119(e) to U.S. Provisional Patent Application No. 61/431,020, filed Jan. 9, 2011, all of which are hereby incorporated by reference in their entireties and to all of which the present application claims priority.

BACKGROUND

Recent consumer interest in personal health has led to a variety of personal health monitoring devices being offered on the market. Such devices, until recently, tended to be complicated to use and were typically designed for use with one activity, e.g., bicycle trip computers.

Due to recent advances in sensor, electronics, and power source miniaturization, fitness monitoring devices currently offered, e.g., Fitbit's activity trackers and other products, greatly simplify the process of tracking health-related data by consumers.

SUMMARY

Details of one or more implementations of the subject matter described in this specification are set forth in the accompanying drawings and the description below. Other features, aspects, and advantages will become apparent from the description, the drawings, and the claims. Note that the relative dimensions of the following figures may not be drawn to scale unless specifically indicated as being scaled drawings.

In some implementations, a method of interacting with a user to promote engagement with a fitness monitoring device configured to measure a fitness parameter of the user is provided. The method may include detecting user engagement with the fitness monitoring device on multiple occasions and receiving a level of engagement metric for the user based, at least in part, on multiple detected user engagements with the fitness monitoring device. In such implementations, each user engagement may produce at least one measurement of the fitness parameter.

In some such implementations, the method may further include generating, from the level of engagement metric, a notification containing information designed to encourage the user to engage with the fitness monitoring device more frequently and/or maintain an existing level of engagement with the fitness monitoring device.

In some such implementations, receiving the level of engagement metric for the user may also include determining the level of engagement metric for the user based, at least in part, on multiple detected user engagements with the fitness monitoring device.

In some implementations, the fitness monitoring device may be a scale and the fitness parameter may be the user's weight. In some such implementations, the scale may be configured to measure the user's weight and percent body fat. In some such implementations, the method may further include determining the user's percent body fat by measuring the impedance between two or more electrodes on the scale.

In some implementations of the method, receiving the level of engagement metric may also include determining the user's frequency of user engagement with the fitness monitoring device.

In some implementations of the method, the method may further include receiving information indicating a change in the user's frequency of user engagement with the fitness monitoring device after generating the notification.

In some implementations of the method, receiving the level of engagement metric may include calculating a weighted moving average based on a plurality of prior user engagement metrics for a plurality of time intervals.

In some implementations of the method, the method may further include receiving a holistic health score determined from one or more of the following parameters associated with the user: a sleep characteristic, a demographic characteristic, a location characteristic, a caloric intake rate, body fat level, step count per unit time, a level of interaction with a second fitness monitoring device, and weight. The method may also further include using the holistic health score, together with the level of engagement metric, to determine the information that is designed to encourage the user to more frequently engage with the fitness monitoring device and/or maintain a level of engagement with the fitness monitoring device.

In some implementations of the method, the holistic health score may be determined from one or more parameters obtained from a second fitness monitoring device or by data provided by via a website in association with an account associated with the person.

In some implementations of the method, the notification may include presenting a congratulatory message for reaching a defined value of the level of engagement metric and/or a defined value of the fitness parameter.

In some implementations of the method, the notification may include presenting a castigatory message for failing to reach a defined value of the level of engagement metric and/or a defined value of the fitness parameter.

In some implementations of the method, the notification may include a message that is sent to a friend or relative of the person.

In some implementations of the method, the notification may include a message to the user presented via a social networking site and visible to people associated with an account of the user on the social networking site.

In some implementations of the method, the notification may include presenting a congratulatory message for meeting a pre-established user engagement goal.

In some implementations of the method, the notification may include granting a gaming asset for a computer-based game to the user and/or taking the gaming asset away from the user. In some implementations, the gaming asset may be an avatar accessory, in-game currency, an in-game unlockable, or downloadable content.

In some implementations of the method, the method may further include determining through the user's level of engagement metric and/or measured fitness parameter that the user has changed a behavior impacting fitness and the notification may include presenting a congratulatory message for changing the behavior that impacts the user's fitness.

In some implementations of the method, the notification may include an audible communication and/or a tactile communication.

In some implementations of the method, the method may further include determining that the level of engagement metric is below a threshold level of engagement, determining the location of the user, and causing the fitness monitoring device to move with respect to the user. In some such implementations, the fitness monitoring device may be caused to move relative to the location of the user. For example, in some implementations, the fitness monitoring device may be caused to move towards the location of the user, whereas in other implementations, the fitness monitoring device may be caused to move away from the location of the user.

In some implementations of the method, the method may further include determining that an alarm clock alarm is to be activated based on data indicating time and providing the notification via the notification mechanism responsive to the determination that the alarm clock alarm is to be activated.

In some such implementations, the method may further include ceasing providing the notification responsive to the user engaging with the fitness monitoring device to produce a measurement of the fitness parameter. For example, the user may cause the notification to cease being provided if they interact with the fitness monitoring device to obtain a measurement of the fitness parameter.

In some implementations of the method, the method may further include measuring the fitness parameter of the user and using the measured fitness parameter to distinguish the user from multiple other users.

In some such implementations of the method, the method may further include storing measured values of the fitness parameter for the user and for the other users, comparing a currently-measured value of the fitness parameter to the stored measured values of the fitness parameters, and determining which user provides the currently-measured value of the fitness parameter based on a correlation between the stored measured values of the fitness parameters for the user and the currently measured value of the fitness parameter.

In some implementations of the method, the method may further include generating multiple notifications of different types, each containing information designed to encourage the user to more frequently engage with the fitness monitoring device and/or maintain a level of user engagement with the fitness monitoring device; determining whether one or more of the types of notifications corresponds to the user's more frequent engagement with the fitness monitoring device; and adjusting the generating of the multiple notifications of different types to promote the more frequent engagement with the fitness monitoring device.

In some implementations, a system may be provided. The system may include one or more processors, a memory, a first biometric sensor, and a notification mechanism. The first biometric sensor may be configured to measure one or more fitness parameters of a first person; the first biometric sensor, the notification mechanism, the one or more processors, and the memory may be communicatively connected; and the memory may store instructions for controlling the one or more processors to: detect user engagement by the first person with the first biometric sensor on multiple occasions, determine a level of engagement metric for the first person based, at least in part, on multiple detected user engagements with the fitness monitoring device, and generate, from the level of engagement metric and using the notification mechanism, a notification containing information designed to encourage the first person to more frequently engage with the first biometric sensor and/or maintain a level of engagement with the first biometric sensor. In such implementations, each user engagement may produce at least one measurement of a fitness parameter using the first biometric sensor.

In some implementations of the system, the first biometric sensor may be housed in a scale and may be configured to at least measure the weight of the first person. In some such implementations, the one or more processors may include at least one processor located in a web server remote from the scale.

In some implementations of the system, the memory may further store instructions for further controlling the one or more processors to determine the level of engagement metric for the first person based at least in part on the first person's frequency of user engagement with the first biometric sensor.

In some implementations of the system, the memory may further store instructions for further controlling the one or more processors to determine a change in the first person's frequency of user engagement with the first biometric sensor after generating the notification.

In some implementations of the system, the memory may further store instructions for further controlling the one or more processors to: determine a holistic health score from one or more of the following parameters associated with the first person: a sleep characteristic, a demographic characteristic, a location characteristic, a caloric intake rate, a level of interaction with a second biometric sensor, and weight; and then use the holistic health score, together with the level of engagement metric, to determine the information designed to encourage the first person to more frequently engage with the first biometric sensor and/or maintain a level of engagement with the first biometric sensor.

In some implementations of the system, the notification may include presenting a congratulatory message for reaching a defined value of the level of engagement metric and/or a defined value of the fitness parameter.

In some implementations of the system, the notification may include a message to a second person associated with the first person.

In some implementations of the system, the notification may include a message to the first person presented via a social networking site and visible to other people associated with an account of the first person on the social networking site.

In some implementations of the system, the notification may include presenting a congratulatory message for meeting a pre-established fitness goal.

In some implementations of the system, the notification may include a castigatory message for failing to meet a pre-established fitness goal.

In some implementations of the system, the memory may further store instructions for further controlling the one or more processors to: determine through the first person's level of engagement metric and/or measured fitness parameter that the first person has changed a behavior impacting fitness, and the notification may include presenting a congratulatory message for changing the behavior impacting fitness.

In some implementations of the system, the notification may include an audible communication and/or a tactile communication.

In some implementations of the system, the memory may further store instructions for further controlling the one or more processors to: determine that the level of engagement metric is below a threshold level of engagement, determine the location of the first person, and cause the first biometric sensor to move with respect to the first person.

In some such implementations of the system, the memory may further store instructions for further controlling the one or more processors to cause the first biometric sensor to move towards the first person.

In some implementations of the system, the memory may further store instructions for further controlling the one or more processors to: determine whether a time-based alarm is to be activated and provide the indication via the notification mechanism responsive to the determination that the time-based alarm is to be activated.

In some implementations, an apparatus may be provided. The apparatus may include a housing; at least one biometric sensor configured to measure at least one fitness parameter of a person associated with the apparatus; a notification mechanism, wherein the notification mechanism is selected from the group consisting of: a visual indicator, a tactile indicator, an audio indicator, an electronic communications interface, and combinations thereof; and a controller including one or more processors and a memory. The one or more processors and the memory may be communicatively connected, and the memory may store instructions for controlling the one or more processors to: receive an instruction to activate the notification mechanism to indicate that the person associated with the apparatus should use the apparatus to obtain a measurement of the at least one fitness parameter using the at least one biometric sensor, and cause, responsive to receiving the instruction, the notification mechanism to provide an indication that the person associated with the apparatus should use the apparatus to obtain a measurement of the at least one fitness parameter using the at least one biometric sensor.

In some such implementations, the apparatus may be a scale and the at least one biometric sensor may include a weight-sensing sensor.

In some implementations of the apparatus, the indication may be provided by an action such as activating a visual indicator on the apparatus, emitting an audible sound, emitting an audible melody, emitting a spoken message, vibrating all or part of the apparatus, causing the apparatus to move, sending a wireless signal to a remote device, or combinations thereof.

In some implementations of the apparatus, the instruction to activate the notification mechanism may be generated, at least in part, in response to a level of engagement metric for the apparatus, wherein the level of engagement metric is determined, at least in part, based on in how many time intervals within a defined time period the person associated with the apparatus has obtained a measurement of the at least one fitness parameter using the apparatus.

In some implementations of the apparatus, the instruction may be received by the one or more processors from a device remote from the apparatus. In some such implementations, the instruction may be received by the one or more processors via a wireless connection and from a device remote from the apparatus.

In some implementations of the apparatus, the apparatus may further include a sensor configured to detect when the person is near the apparatus and the memory may further store instructions for further controlling the one or more processors to cause the notification mechanism to provide the indication that the person should use the apparatus to obtain the measurement of the at least one fitness parameter using the at least one biometric sensor when the sensor indicates that the person is near the apparatus. In some such implementations of the apparatus, the sensor may be a microphone, an accelerometer, a camera, a motion sensor, a $CO_2$ sensor, a particle counter, or combinations thereof.

In some implementations of the apparatus, the sensor may be a wireless receiver and may be configured to determine that the person is near the apparatus by, at least in part, receiving a wireless signal from a device worn or carried by the person.

In some implementations of the apparatus, the apparatus may be a scale and the at least one biometric sensor may include a weight-sensing sensor. In such implementations, the apparatus may further include a locomotive drive mechanism configured to move the apparatus across a floor and the memory may store further instructions for further controlling the one or more processors to control the locomotive drive mechanism to move the apparatus relative to the person.

In some such implementations of the apparatus, the instructions for further controlling the one or more processors to control the locomotive drive mechanism to move the apparatus relative to the person control the locomotive drive mechanism to move the apparatus towards the person. In some additional or alternative such implementations of the apparatus, the instructions for further controlling the one or more processors to control the locomotive drive mechanism to move the apparatus relative to the person control the locomotive drive mechanism to move the apparatus away from the person.

In some implementations of the apparatus, the memory may store further instructions for further controlling the one or more processors to control the notification mechanism to emit an audible sound or a pre-recorded or synthesized voice message encouraging the person to weigh themselves using the apparatus.

In some implementations of the apparatus, the memory may store further instructions for further controlling the one or more processors to: determine a current time of day, determine that the current time of day correlates with a pre-set alarm time, and provide the indication via the notification mechanism responsive to the determination that the current time of day correlates with the pre-set alarm time.

In some such implementations of the apparatus, the memory may store further instructions for further controlling the one or more processors to cancel the indication in response to the person associated with the apparatus using the apparatus to obtain the measurement of the at least one fitness parameter using the at least one biometric sensor.

In some such implementations of the apparatus, the indication may be a wireless signal sent by the apparatus to a remote device and the instructions for controlling the one or more processors to cancel the indication cause the apparatus to send a second wireless signal to the remote device indicating that the indication is to be canceled.

These and other implementations are described in further detail with reference to the Figures and the detailed description below.

BRIEF DESCRIPTION OF THE DRAWINGS

The various implementations disclosed herein are illustrated by way of example, and not by way of limitation, in the figures of the accompanying drawings, in which like reference numerals may refer to similar elements.

DETAILED DESCRIPTION

Figure 1:
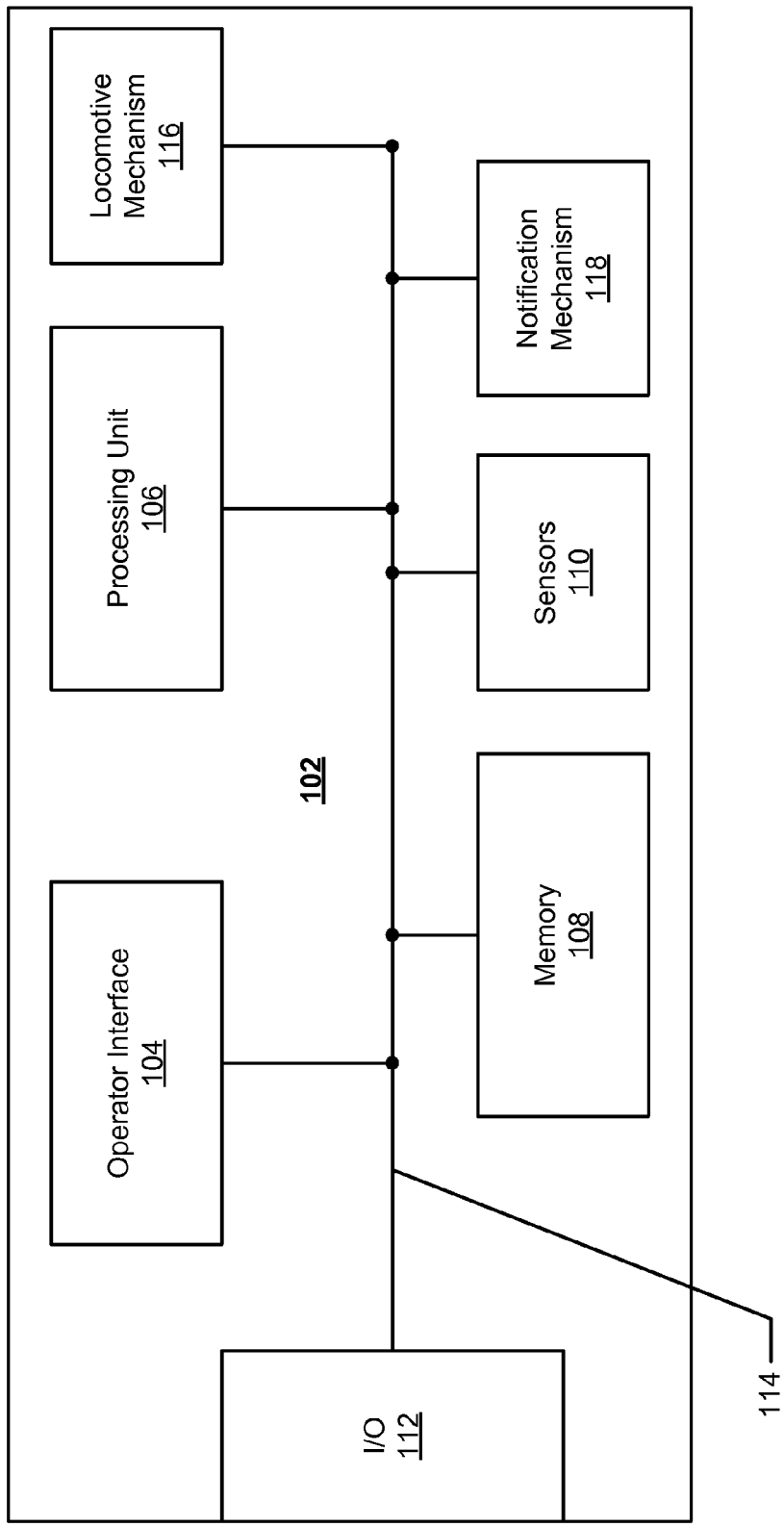
FIG. 1 depicts a functional schematic for a fitness monitoring device.

The present inventors have realized that the advent of consumer-oriented fitness monitoring devices such as wireless weight scales and activity trackers has led to widespread adoption of voluntary self-monitoring and data collection by consumers, enabling intervention-less experiments on behavioral modification that were previously impossible or impractical. For example, Fitbit, Inc., fitness monitoring devices, including wearable fitness/activity trackers and wireless body weight scales, collect large amounts of data on individuals' health and activity habits entirely without external prompting by experimenters. As a result, the present inventors studied a large volume of data resolved to the level of a single user, and have determined that there is, under circumstances, an observable correlation between an individual's weight loss and the frequency with which they check their weight with advanced weight-monitoring devices.

Accordingly, the present inventors have determined that increased voluntary, unprompted usage of a body weight scale, such as Fitbit's Aria, correlates with increased overall fitness and increased weight loss, either through increased activity (caloric burn), healthier diet (less caloric intake), or both. This is notable in the context of a device such as the Aria since the Aria does not track activity, but only tracks weight and body fat percentage. The present inventors have discovered that increasing voluntary user engagement with fitness monitoring devices, such as with weight scales, may cause users to also become more actively engaged with their health and to consequently experience greater success in terms of leading healthier lifestyles. The present inventors have also discovered that there is a benefit to encouraging increased user engagement with fitness monitoring devices in general, e.g., fitness monitoring devices other than body weight scales.

To be clear, while many of the examples provided herein are directed at fitness monitoring devices in the form of a body weight scale, the correlation between high frequency of engagement with a fitness monitoring device and increased fitness/weight loss is to be understood to extend to all types fitness monitoring devices, including to fitness monitoring devices that are "continuous" monitoring devices, e.g., wearable activity trackers that collect data continuously, as well as to "intermittent" monitoring devices, e.g., scales and other devices that are not worn by a person but that may be interacted with sporadically by a person in order to track "slow" data, i.e., data where continuous sampling is unnecessary due to the low speed with which that data may change. It is also to be understood that, with respect to wearable continuous monitoring devices, user engagement may be defined as including both the simple act of wearing such devices and the more involved act of deliberately interacting with the devices, e.g., pushing a button in order to view a measured fitness parameter. The former may be referred to herein as "passive user engagement," and the latter may be referred to herein as "active user engagement." "Active user engagement" may also be used to describe the engagement of a person with an intermittent monitoring device in order to obtain a fitness parameter measurement. Generally speaking, the techniques described herein may be used with either type of user engagement.

"User engagement," as used herein with respect to a person's "user engagement" with a particular fitness monitoring device or biometric sensor, refers to an interaction of the person with the fitness monitoring device or a biometric sensor in such a way that the fitness monitoring device or biometric sensor produces a measurement of a fitness parameter for that person. In some cases, a fitness monitoring device or biometric sensor may generally remain in a location separate from a person, and the person may need to approach the fitness monitoring device or biometric sensor and actively interact with it in order to "engage" with the fitness monitoring device or biometric sensor, e.g., stepping on a floor scale to take a weight measurement. In other cases, the fitness monitoring device or biometric sensor may be designed to be worn by the person, in which case the person may be "engaged" with the fitness monitoring device or biometric sensor as long as they are wearing it or, in some cases, by probing, interrogating, or otherwise deliberately interacting with the fitness monitoring device or biometric sensor.

The present inventors have discovered that a "level of engagement metric," which is a measure of how "engaged" a person is with a fitness monitoring device or biometric sensor, may provide valuable insight to the person's behavior and serve as a prompt for actions to be taken that may increase user health through increased user engagement with the fitness monitoring device or biometric sensor. The level of engagement metric may serve as a normalized or standardized metric across a large population of people that use fitness monitoring devices or biometric sensors. The level of engagement metric may be determined through a variety of techniques, although, regardless of technique, the level of engagement metric may be viewed as indicative of how frequently a specific person interacts with the device in question or how excited or interested that person is in the device.

In some implementations, the level of engagement metric may be calculated based on the number of user engagements with a fitness monitoring device or biometric sensor over a period of time. For example, a person who uses a fitness monitoring device or biometric sensor on 5 out of 7 days in a week may have a level of engagement metric for the week that is approximately 0.71. However, other techniques for calculating a level of engagement metric for the person may be used as well, including using different time periods, different intervals, the intensity of engagement in one or more intervals, and so forth. The level of engagement metric for a person may also be influenced by factors that do not result from direct engagement with the fitness monitoring device or biometric sensor, but that otherwise indicate that the person is actively interested in/aware of the fitness monitoring device or biometric sensor. For example, if a person mentions the fitness monitoring device or biometric sensor on a social networking site or in an email, that may be factored into the level of engagement metric as indicating a higher level of engagement.

Generally speaking, the level of engagement metric may take on any of a variety of forms, but may reflect certain basic characteristics. For example, the level of engagement metric typically relates a number of actual "user engagements" to a number of opportunities for "user engagement." The level of engagement metric often presents a ratio of these two quantities. The exact form of the level of engagement metric may vary from user to user, and between different groups to which a user belongs, e.g., demographic groups may utilize different rules to calculate a level of engagement metric, and a person may be a member of multiple demographic groups.

The quantities used to calculate a level of engagement metric may be simple counts, e.g., evaluations of whether a user engagement occurred/did not occur within a given opportunity for engagement, that are unaffected by other considerations, such as the type of user engagement or the time of the user engagement.

Other quantities used to calculate the level of engagement metric may be weighted such that some user engagements or opportunities for engagement contribute more to the level of engagement metric than others. Weighting may be based on day (of week, year, weather condition, etc.) or recentness of the user engagement or opportunity for engagement.

Once a level of engagement metric for a person with respect to a fitness monitoring device has been determined, a decision may be made as to whether or not action should be taken to attempt to increase the person's user engagement with the fitness monitoring device. In some implementations, this may include deciding whether or not action should be taken to maintain a person's level of user engagement with the fitness monitoring device.

For example, if a person uses a fitness monitoring device, e.g., a body weight scale, twice a week, they may have a comparatively low level of engagement metric as compared with people who also use the same type of fitness monitoring device daily. A decision may be made that an attempt should be made to alter the person's behavior such that they more frequently engage with the fitness monitoring device (thus increasing their level of engagement metric).

If an attempt is made to alter the person's engagement with a fitness monitoring device, such an attempt may take any of a number of forms. The particular form used may be selected based on a variety of factors, including the forms of past attempts that appear to have been successful (or unsuccessful) in provoking the desired change in engagement for the person, which forms of attempts have been successful (or unsuccessful) as a whole across a demographic group to which the person belongs, etc.

These attempts may, in the context of this disclosure, take the form of a "notification;" the mechanism through which the notification may be conveyed may, generally speaking, be referred to as a notification mechanism. A notification (or indication), as used herein, is, unless otherwise indicated by the context, a communication that is initiated with the intention of encouraging a person to engage more frequently with a fitness monitoring device or biometric sensor. Notifications may be provided through a variety of media, and may, in some cases, require further action by an intermediate device before being perceptible by the person. For example, a fitness monitoring device or biometric sensor may have a notification mechanism that includes a display or lights that are configured to display graphics or light up in order to catch the attention of a person (the notification, in this case, may refer to a signal that is sent to the lights or display that cause these components to light up or display graphics to a person; it may also refer to the light or graphics that is emitted or displayed by components receiving the signal in response to the signal). In some examples, the fitness monitoring device or biometric sensor may have a notification mechanism that includes a speaker or other device capable of generating auditory output that may be used to provide the notification (the notification in this case may be a signal that is sent to a speaker or other audio device; it may also refer to the actual audio output that is generated by the audio device in response to the signal. In some other or additional examples, the notification mechanism may include a wireless interface and the notification may take the form of an electronic or electromagnetic communication, e.g., a wireless signal, that is sent to another device, e.g., a wearable fitness monitoring device such as a Fitbit activity tracker or a smartphone, associated with the person (the notification in this case may be an electromagnetic signal; it may also refer to any audio, visual, tactile, or other output generated by the receiving device in response to receipt of the signal). In such scenarios, the notification may still be generated or initiated by the notification mechanism even if the intended recipient device of the communication fails to be activated or otherwise fails to convey the notification to the person.

FIG. 1 depicts a generalized schematic of an example fitness monitoring device or other device with which the various operations described herein may be executed, either in whole or in part. The fitness monitoring device 102 may include a processing unit 106 having one or more processors, a memory 108, an operator interface 104, one or more biometric sensors 110 (e.g., a load cell or strain gauge used for measuring weight, electrodes for measuring body fat percentage, accelerometers for measuring movement, etc.), input/output 112, a locomotive mechanism 116, and a notification mechanism 118. The processing unit 106, the memory 108, the operator interface 104, the one or more biometric sensors 110, the locomotive mechanism 116, and the input/output interface 112 may be communicatively connected via communications path(s) 114 (it is to be understood that some of these components may also be connected with one another indirectly). One or more of these components or systems may be omitted from some implementations if the functionality provided by them is not needed, e.g., the locomotive mechanism may be omitted if the fitness monitoring device does not need to be capable of self-directed movement.

The fitness monitoring device may collect one or more types of fitness parameter data, e.g., data pertaining to physical characteristics of the human body (such as weight, body fat percentage, heartbeat, perspiration levels, etc.) and/or data relating to the physical interaction of that body with the environment (such as accelerometer readings, gyroscope readings, etc.), from the one or more biometric sensors 110 and/or external devices (such as an external heart rate monitor, e.g., a chest-strap heart rate monitor) and may then store such information for later use, e.g., for communication to another device via the I/O interface 112, e.g., a smartphone or to a server over a wide-area network such as the Internet. The processing unit 106 may also perform an analysis on the stored data and may initiate various actions depending on the analysis. Alternatively or additionally, one or more processors located external to the fitness monitoring device may analyze the data, e.g., a server or cloud-based data handling system may analyze the data and then communicate results back to the fitness monitoring device (or send instructions based on the results back to the fitness monitoring device).

In general, fitness monitoring devices may incorporate one or more types of user interfaces including but not limited to visual, auditory, touch/vibration, or combinations thereof. The fitness monitoring device may, for example, display information relating to one or more of the data types available and/or being tracked by the fitness monitoring device through, for example, a graphical display or through the intensity and/or color of one or more LEDs. The user interface may also be used to display data from other devices or internet sources. The device may also provide haptic feedback through, for instance, the vibration of a motor or a change in texture or shape of the device. In some implementations, the biometric sensors themselves may be used as part of the user interface, e.g., accelerometer sensors may be used to detect when a person taps the housing of the fitness monitoring device with a finger or other object and may then interpret such data as a user input for the purposes of controlling the fitness monitoring device. For example, double-tapping the housing of the fitness monitoring device may be recognized by the fitness monitoring device as a user input that will cause the display of the fitness monitoring device to turn on from an off state or that will cause the fitness monitoring device to transition between different monitoring states, e.g., from a state where the fitness monitoring device may interpret data according to rules established for an "active" person to a state where the fitness monitoring device may interpret data according to rules established for a "sleeping" person. In another example, standing on a body weight scale may cause the body weight scale to enter an "active" mode where it attempts to obtain a fitness parameter measurement—a load cell used to obtain the measurement may also be used as a switch to cause the body weight scale to enter the active mode.

While the user is using, i.e., engaged with, the fitness monitoring device 102, the fitness monitoring device 102 may calculate or measure and store a fitness parameter, e.g., weight and/or body fat percentage and then subsequently transmit data representative of the fitness parameter to the user's account on a web service like www.Fitbit.com, to a mobile computational device, e.g., a phone, paired with the fitness monitoring unit, and/or to a standalone computer or server where the data may be stored, processed, and visualized by the user. Such transmission may be carried out via communications through I/O interface 112. Various fitness monitoring devices that may be used with the techniques discussed herein may measure or calculate fitness parameters that include, but are not limited to, caloric energy expenditure, floors climbed or descended, heart rate, heart rate variability, heart rate recovery, location and/or heading (e.g., through GPS), elevation, ambulatory speed and/or distance traveled, swimming lap count, bicycle distance and/or speed, blood pressure, blood glucose, skin conduction, skin and/or body temperature, electromyography data, electroencephalographic data, weight, body fat, and respiration rate. The device may also measure or calculate metrics related to the environment around the user such as barometric pressure, weather conditions, light exposure, noise exposure, and magnetic field.

As mentioned previously, collected fitness parameter data from the fitness monitoring device may be communicated to external devices through the communications or I/O interface 112. The I/O or communications interface may include wireless communication functionality so that when the fitness monitoring device comes within range of a wireless base station or access point, the stored data automatically uploads to an Internet-viewable source such as a website, e.g., www.Fitbit.com. The wireless communications functionality may be provided using one or more communications technologies known in the art, e.g., Bluetooth, RFID, Near-Field Communications (NFC), Zigbee, Ant, optical data transmission, etc. The fitness monitoring device may also contain wired communication capability, e.g., USB. The external device or devices, e.g., a server or cloud computing system, may then analyze the data according to the techniques described herein.

Other implementations regarding the use of short range wireless communication are described in U.S. patent application Ser. No. 13/785,904, titled "Near Field Communication System, and Method of Operating Same" filed Mar. 5, 2013 which is hereby incorporated herein by reference in its entirety.

It is to be understood that FIG. 1 illustrates a generalized implementation of a fitness monitoring device 102 that may be used to implement a fitness monitoring device or other device in which the various operations described herein may be executed. It is to be understood that in some implementations, the functionality represented in FIG. 1 may be provided in a distributed manner between, for example, a chest-strap heart rate sensor may communicate with a separate fitness monitoring device worn elsewhere.

Moreover, it is to be understood that in addition to storing program code for execution by the processing unit to effect the various methods and techniques of the implementations described herein, the memory 108 may also store configuration data or other information used during the execution of various programs or instruction sets or used to configure the fitness monitoring device. The memory 108 may also store fitness parameter data collected by the fitness monitoring device. It is to be further understood that the processing unit may be implemented by a general or special purpose processor (or set of processing cores) and thus may execute sequences of programmed instructions to effectuate the various operations associated with obtaining fitness parameter data, as well as interaction with a user, system operator or other system components. In some implementations, the processing unit may be an application-specific integrated circuit.

Though not shown, numerous other functional blocks may be provided as part of the fitness monitoring device 102 according to other functions it may be required to perform, e.g., environmental sensing functionality, etc. Other functional blocks may provide wireless telephony operations with respect to a smartphone and/or wireless network access to a mobile computing device, e.g., a smartphone, tablet computer, laptop computer, etc. The functional blocks of the fitness monitoring device 102 are depicted as being coupled by the communication path 114 which may include any number of shared or dedicated buses or signaling links. More generally, however, the functional blocks shown may be interconnected using a variety of different architectures and may be implemented using a variety of different underlying technologies and architectures. With regard to the memory architecture, for example, multiple different classes of storage may be provided within the memory 108 to store different classes of data. For example, the memory 108 may include non-volatile storage media such as fixed or removable magnetic, optical, or semiconductor-based media to store executable code and related data and/or volatile storage media such as static or dynamic RAM to store more transient information and other variable data.

The locomotive mechanism 116 may be used to cause the fitness monitoring device 102 to independently move about, e.g., similar to how a Roomba™ vacuum cleaner may navigate about a room. The locomotive mechanism may include some form of mechanical drive that may provide power to wheels, treads, or other mechanisms that may be used to move the fitness monitoring system about—such a mechanism may, for example, be used in a fitness monitoring system such as that described with respect to FIG. 12. The locomotive mechanism 116 may, in addition to a motor or motors and wheels or treads, include a controller with one or more processors and a memory that stores instructions for controlling the motor or motors to cause the fitness monitoring device to move about.

The notification mechanism 118 may be configured to generate and/or provide one or more notifications to a user, and may include one or more components that may be used to generate audio, visual, tactile, electromagnetic, or other types of notifications.

Figure 3:
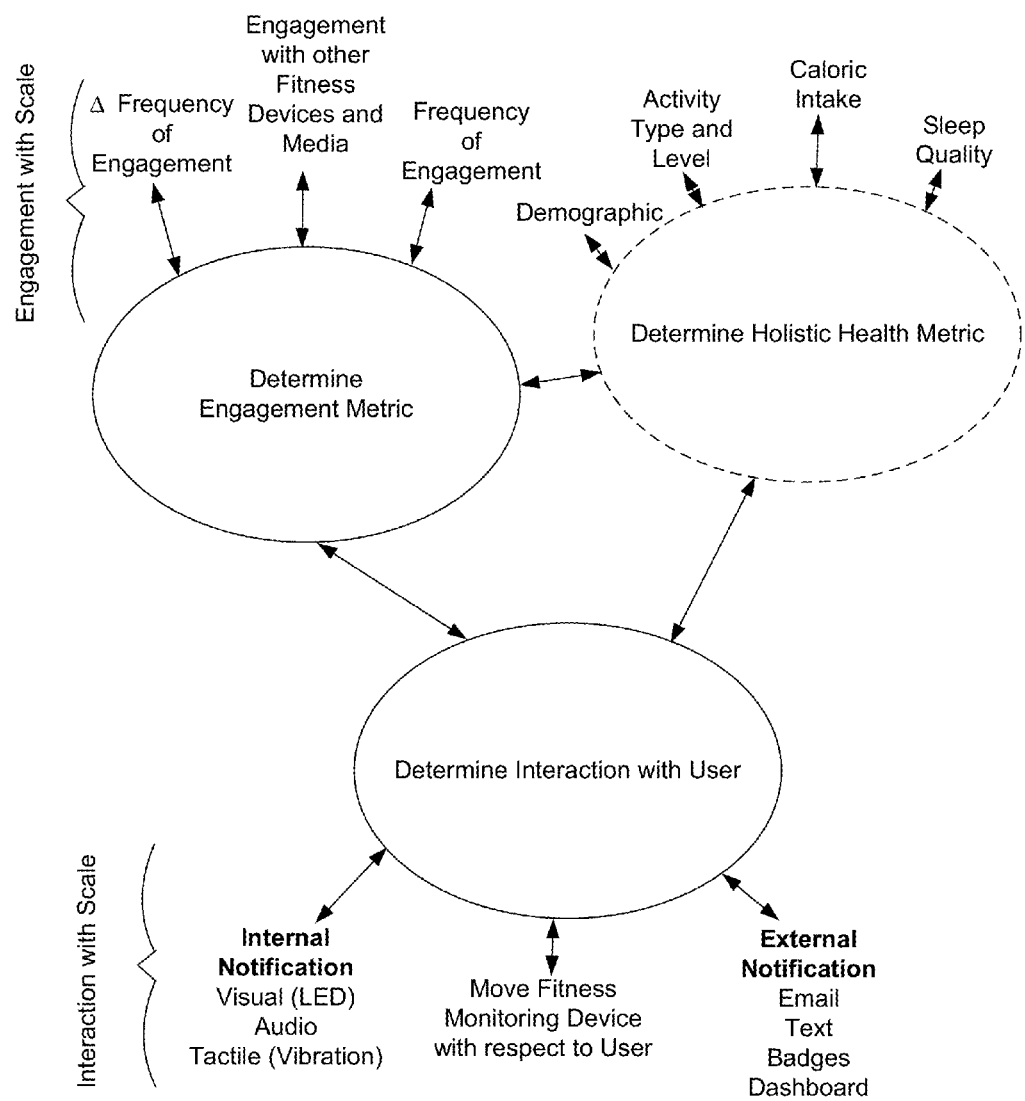
FIG. 3 depicts a framework for certain implementations of an engagement and interaction process using a fitness monitoring device such as a body weight scale.

FIG. 3 presents a conceptual framework for certain embodiments disclosed herein. At one level, a fitness monitoring device and/or an associated component such as a server or mobile computing device receives engagement input 303 such as the frequency of engagement with the fitness monitoring device, a change in the frequency of engagement with the fitness monitoring device (or some other function of the frequency of engagement), and engagement with one or more other fitness devices or fitness media (e.g., a social media service having a fitness component). Other types of input are described elsewhere herein. The fitness monitoring device and/or associated component buffer or store these inputs and under defined triggering conditions calculate a value of the engagement metric as illustrated a 305. As explained elsewhere herein, the engagement metric may have many different forms depending on the independent variables (inputs) employed and the importance attached to each such variable. Optionally, the fitness monitoring device and/or associated component also calculates a holistic health metric 307 from inputs selected because they are relevant to the engagement metric. Example input categories include the following characteristics of the fitness monitoring device's user: demographic, activity level, caloric intake, and sleep quality. Other types of input are described elsewhere herein. A holistic health metric, as used herein, refers to a health score or metric that may incorporate multiple characteristics of a person and/or their behavior in order to arrive at a metric indicative of the person's state-of-health.

The process uses the engagement metric and optionally the holistic health metric to determine whether an action is to be taken (and, in some implementations, the nature of the action) by the fitness monitoring device (or associated component). See block 309. The action is typically a direct interaction with the device user. See interactions 311. In various implementations, the interaction is chosen to encourage the user to engage more frequently and/or productively with the fitness monitoring device. The interaction may also be chosen to encourage other healthful user behaviors. Examples of interactions include user notifications such as an "internal" notification such as visual, audio, or tactile output from the scale or other fitness monitoring device, and an "external" notification such as email messages, text messages or badges provided to the user. Another example of an external notification is an update to the user's fitness dashboard, e.g., such as may be provided via a personal fitness website such as fitbit.com or via an app associated with the user's smartphone or tablet, presented via a computational device. In some embodiments, the fitness monitoring device interacts with the user by moving with respect to the user (e.g., toward or away from the user to encourage a type of engagement with the user). Further examples of such interactions are presented elsewhere herein.

Figure 2:
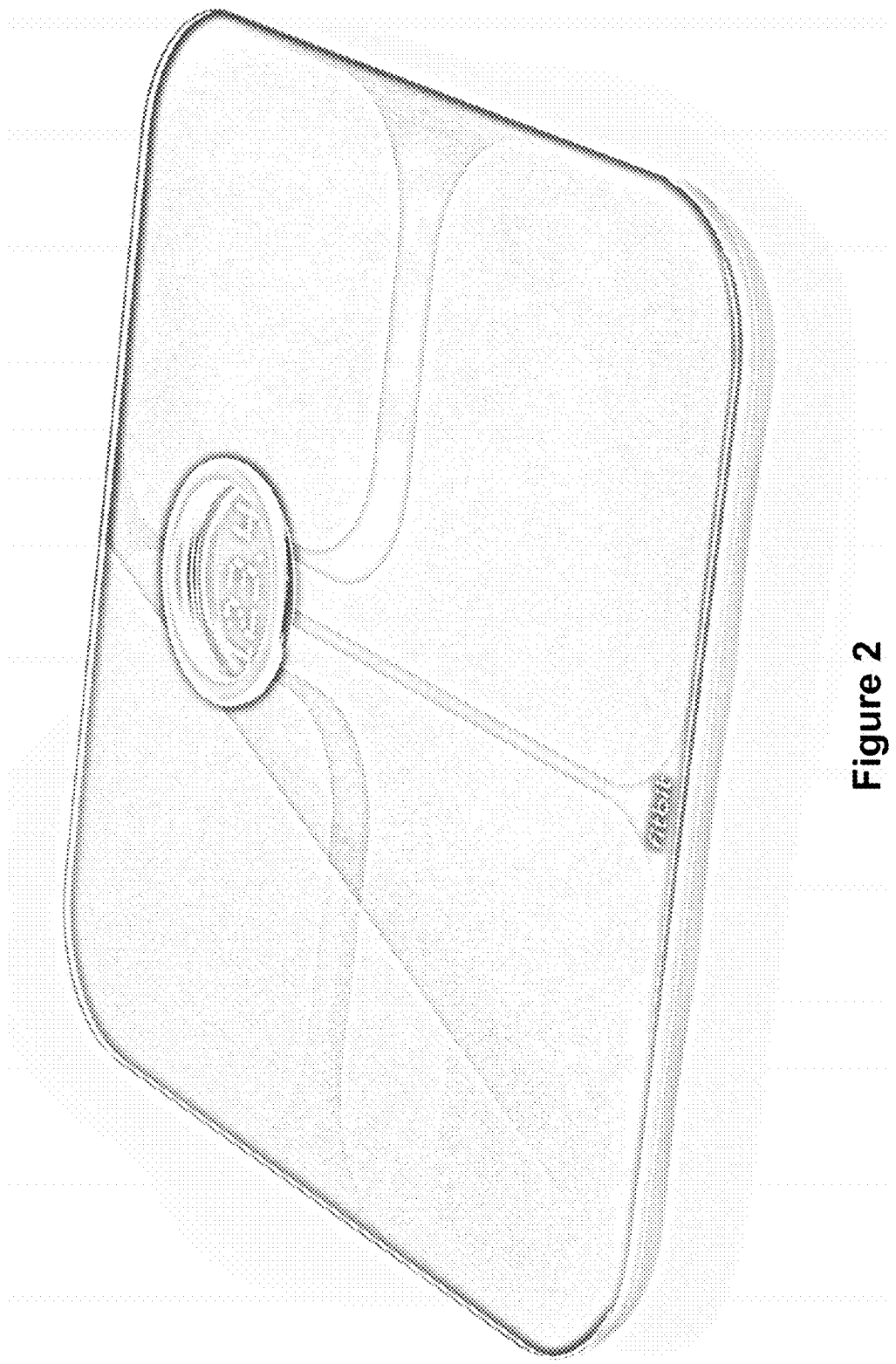
FIG. 2 depicts an image of a Fitbit Aria™ body weight scale.

One example of a fitness monitoring device is a Fitbit Aria™ body weight scale, which is shown in FIG. 2. The Aria™ is capable of turning on when a user steps on it, measuring the user's weight and body fat percentage, determining which person among a pool of people that are registered with the scale is associated with the measurements, and then uploading the measurements to a central server, e.g., fitbit.com, in association with that person.

The various methods and techniques disclosed herein may be implemented through execution of one or more a sequences of instructions, e.g., software programs, by the processing unit 106 or by a custom-built hardware ASIC (application-specific integrated circuit) or programmed into a programmable hardware device such as an FPGA (field-programmable gate array), or any combination thereof within or external to the processing unit 106. In addition to a fitness monitoring device such as that described in FIG. 1, a remote computing system, e.g., a server, cloud-based service provider, or other computing system, may be used to implement portions of the various techniques described herein. For example, a fitness monitoring device may only store a limited quantity of fitness parameter data, and historical fitness parameter data may be maintained in a cloud storage environment—in order to calculate some of the metrics discussed herein, it may be necessary to access the historical fitness parameter data and analyze it, which may be more conveniently performed by a portion of the cloud storage environment, e.g., cloud processing.

Further implementations of fitness monitoring devices can be found in U.S. patent application Ser. No. 13/156,304, titled "Portable Biometric Monitoring Devices and Methods of Operating Same" filed Jun. 8, 2011, which is hereby incorporated herein by reference in its entirety.

Figure 4:
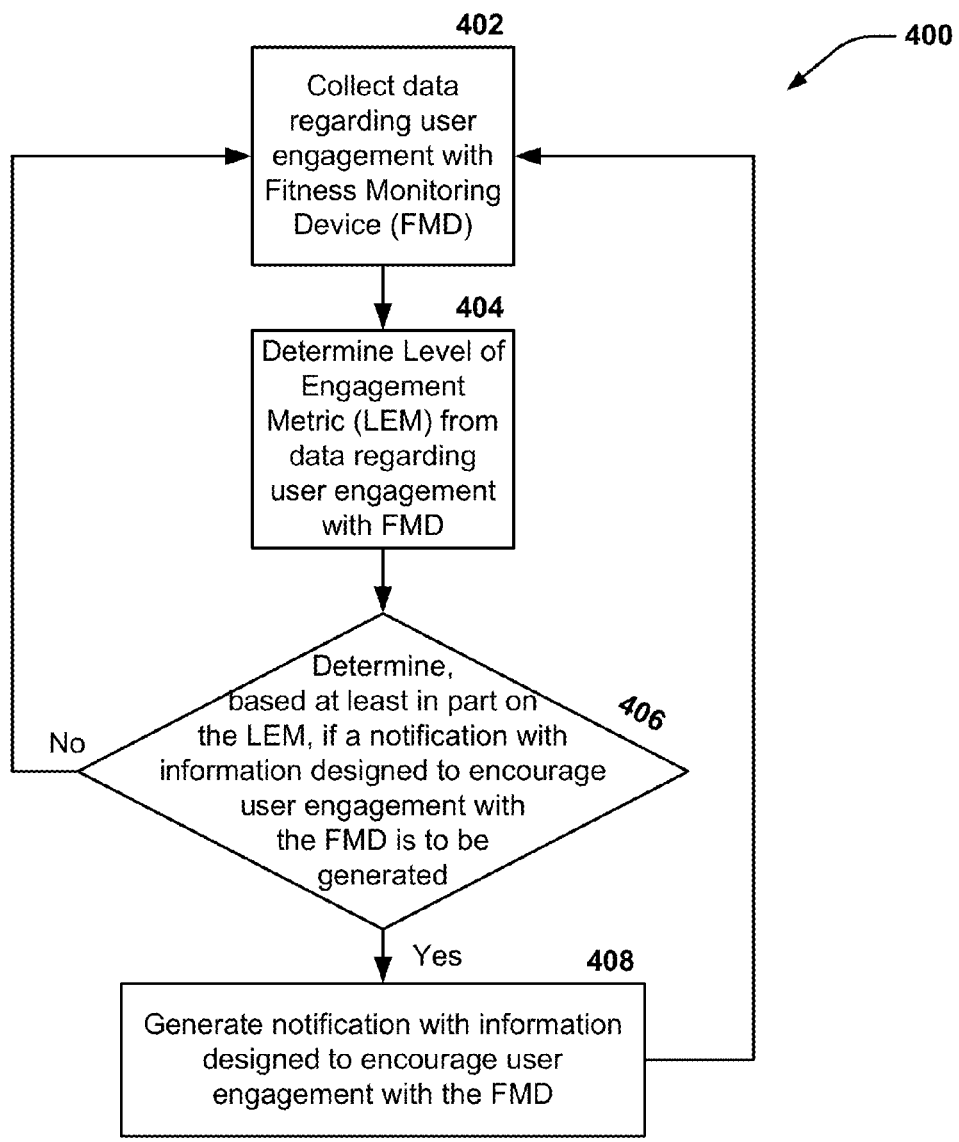
FIG. 4 depicts a flow diagram for a technique for determining how engaged a person is with a fitness monitoring device.

FIG. 4 depicts a flow diagram for a technique for determining how engaged a person is with a fitness monitoring device. The technique 400 begins in block 402, where data regarding user engagement with a fitness monitoring device for a particular person may be collected. Such data may be mined from existing data sources, e.g., historical fitness parameter data may be analyzed to determine past user engagement with the fitness monitoring device.

For example, weight measurement data obtained by a body weight scale may be filtered such that only data for a particular person is considered, and then the timestamps of each measurement may be reviewed to see on which days that person used the body weight scale.

In block 404, a level of engagement metric may be determined for the particular person based on user engagement data obtained in block 402. There may be many ways of determining a level of engagement metric, and such metrics may take a number of forms, all of which are to be recognized as falling within the scope of this disclosure. Generally speaking, as discussed above, a level of engagement metric indicates, in some quantifiable manner, the level of engagement of a person with a fitness monitoring device. The level of engagement metric is not to be confused with other metrics, e.g., the actual fitness parameter or parameters that are measured by the fitness monitoring device.

Various examples of level of engagement metric determination are discussed further with reference to some of the following Figures. A level of engagement metric may be normalized, e.g., ranging between 0 and 1, to allow the level of engagement metric to be compared across a population of users and to allow for more meaningful data comparisons to be made. In other implementations, the level of engagement metric may be absolute, e.g., a constantly incremented score that reflects all user engagements with a fitness monitoring device over the lifetime of the fitness monitoring device. In some implementations, multiple types of level of engagement metrics for a person with respect to a fitness monitoring device may be determined and tracked simultaneously and used for different purposes.

Generally speaking, the use of "receive" with respect to a level of engagement metric (or other parameter/metric discussed herein) may refer to both the receipt of such data from a remote source, e.g., from a server remote from the device or system receiving the data, or may refer to local determination of the data, e.g., a determination of such data within the device or system receiving the data, unless otherwise indicated by the context of the term.

In block 406, a determination may be made based on the level of engagement metric as to whether or not a notification with information designed to encourage increased user engagement with the fitness monitoring device by the person is to be generated. The determination may, for example, be that the level of engagement metric is too low (as compared with a level of engagement metric that is correlated with increased user health), and that increasing user engagement with the fitness monitoring device may cause a concomitant increase in user health. In other scenarios, however, the person may have a level of engagement metric that indicates that increased user engagement may have little effect (for example, a person who is already monitoring their weight on a daily basis may derive little benefit from weighing themselves on a more-than-daily basis), and a notification may not be generated. In some such scenarios, however, it may be determined that a notification should still be generated in order to encourage the person to maintain the level of user engagement with the fitness monitoring device that they currently have. If it is determined in block 406 that no notification is to be generated, the technique may return to block 402. If it is determined in block 406 that a notification is to be generated, such a notification may be generated in block 408 and the technique may then return to block 402.

Such notifications may take any of a number of forms. In some implementations, the notification may take the form of a virtual "badge" or "achievement" that is awarded to the person when the person reaches a predetermined level of engagement metric value. For example, if the level of engagement metric indicates that the person has used the fitness monitoring device at least once on each of 30 consecutive days, the notification may take the form of a badge that indicates that the person has completed a "1 month streak!" or other such achievement (for example, engaging with a fitness monitoring device on each of predetermined number, e.g., 5, 10, 20, 30, etc.) of consecutive time periods (e.g., days, weeks, months, years). Having received such an achievement, the person may then be motivated to attempt to achieve another such achievement (or to attempt to achieve achievements having higher requirements for being earned). In the case of badge or achievement notifications, the notification may be designed to indirectly encourage increased user engagement on behalf of the person by rewarding increased engagement, i.e., rewarding positive behavior.

In other implementations, the notification may be designed to more directly encourage the person to increase their user engagement with the fitness monitoring device. For example, the notification may take the form of a message that is sent to the user, e.g., via their smartphone, email, social networking account, or the fitness monitoring device itself, that suggests to the person that they use the fitness monitoring device to obtain a fitness parameter measurement using the fitness monitoring device. Such a message may be congratulatory (to recognize positive behavioral choices) or castigatory or taunting (to recognize poor behavioral choices). In some implementations, the notification may additionally or alternatively be sent to a third party that is associated with the person, e.g., a parent, spouse, or friend (the person may designate the third party). For example, the notification may be a message such as "Adam hasn't weighed himself in the last 3 days, can you please remind him to do so?" that is sent to Adam's mother. This may prompt Adam's mother to call or email her son and encourage him to use the fitness monitoring device. In this manner, the notification may be designed to be conducive to triggering peer pressure on the person to improve their user engagement with the fitness monitoring device.

Another variant of a notification that is designed to encourage increased user engagement with a fitness monitoring device through peer pressure may utilize a message that is posted to a publicly-accessible (at least, accessible to one or more peers of the person) area of a social networking website (or other public forum, e.g., Twitter) such that peers of the person may see the message. The person's peers may, as is often human nature, provide encouragement to the person to increase their user engagement with the fitness monitoring device. Such encouragement may, of course, take a variety of forms, depending on the nature of the person's peers—it may range from positive reinforcement to good-natured mockery to outright scolding. Typically, a person's peers will have a better sense of what sort of repartee is most effective in getting the person to change their behavior than may be deduced by an automated system. Moreover, the person is more likely to give weight to a peer's suggestions/encouragement than to suggestions/encouragement that is provided by an automated system.

The system may be configured to allow a person to specify the media through which notations may be delivered, e.g., the person may instruct the system to provide notifications through Facebook postings since they will be publicly visible to friends of the person, and the person knows that the only way they will be motivated to engage more frequently with a fitness monitoring device is if there is the threat of their friends witnessing their failure to do so.

In some implementations, the notification may be delivered, at least in part, in by a video game system played by the person. For example, the person may be a user of Xbox Live™, which features avatars for each user that may be customized with costumes, clothes, and accessories. A notification may take the form of a new set of clothes or a costume that is unlocked for use with the avatar; the person may be motivated to continue to engage with the fitness monitoring device in the hopes of receiving further such "unlockable" video game console assets. In some such implementations, the notification may be delivered as virtual currency, items, equipment, or other assets to be used in an actual video game. For example, a person who uses a video game system to play sports games that involve actual movement by the player, e.g., such as the Nintendo Wii™ or the Xbox 360 Kinect™, may receive an extra mini-game as a form of notification. Such gaming-oriented notification options may also be applied to non-console environments, e.g., to avatars on a social networking site.

In some implementations, the notification may be provided in conjunction with a communication from another system, such as an alarm clock. For example, in some implementations discussed later below, a fitness monitoring device may either serve as an alarm clock or communicate with a device serving as an alarm clock, e.g., a smartphone. When the alarm clock alarm goes off, the fitness monitoring device may cause the alarm clock alarm to remain on until the person has measured a fitness parameter on the fitness monitoring device if the level of engagement metric indicates that a notification is to be generated. Thus, the fact that the alarm does not turn off until the person weighs themselves may serve as the notification (the alarm would be triggered regardless of the level of engagement metric, but the level of engagement metric may determine how the alarm may be turned off).

In some other implementations, the notification may be provided through other mechanisms. For example, in one example discussed below, a fitness monitoring device such as a body weight scale may have some locomotive mechanism for moving the fitness monitoring device around, e.g., wheels on the underside, and a suite of sensors that allows the fitness monitoring device to determine when a person or, in some implementations, a particular person is in close proximity, e.g., in the same room, within a certain distance, visible to sensors on the fitness monitoring device, etc., to the fitness monitoring device. If the level of engagement metric for that person (or for a person associated with the fitness monitoring device) results in a notification being generated, the notification may cause the locomotive mechanism to move the fitness monitoring device towards the person. The present inventors have realized that a fitness monitoring device, e.g., a body weight scale, that moves towards a person may be much more difficult for the person to ignore, especially if combined with other forms of notification discussed elsewhere in this disclosure.

In various implementations, the notification may ultimately be provided using any of a variety of output mechanisms, i.e. notification mechanisms. In some implementations, the notification may include nothing more than a light on the fitness monitoring device that blinks intermittently when a person associated with the fitness monitoring device has a level of engagement metric that causes a notification to be generated. In other additional or alternative implementations, the notification may include other visual feedback, e.g., graphics, text on a display, etc.; audio feedback, e.g., melodies, speech, sound effects, etc.; tactile feedback, e.g., vibration, mild electric shock, etc.; electromagnetic signals to other devices to cause those other devices to provide feedback perceptible to the person, e.g., signals sent to smartphones, laptops, desktops, tablets, other fitness monitoring devices, etc.; and other forms of communicating with the person.

Generally speaking, while some of the notifications discussed herein may not be discussed as being implemented in conjunction with other types of notifications disclosed herein, the various notifications discussed herein may, generally speaking, be implemented in combination with one or more other types of notifications.

As discussed above, a level of engagement metric may be calculated in a number of ways, and there may be multiple level of engagement metrics, each calculated using a different technique and used in a different way in order to determine whether or not a notification is to be generated (or for some other purpose). Some example techniques for calculating a level of engagement metric are discussed with reference to FIGS. 5 through 8 below.

Figure 5:
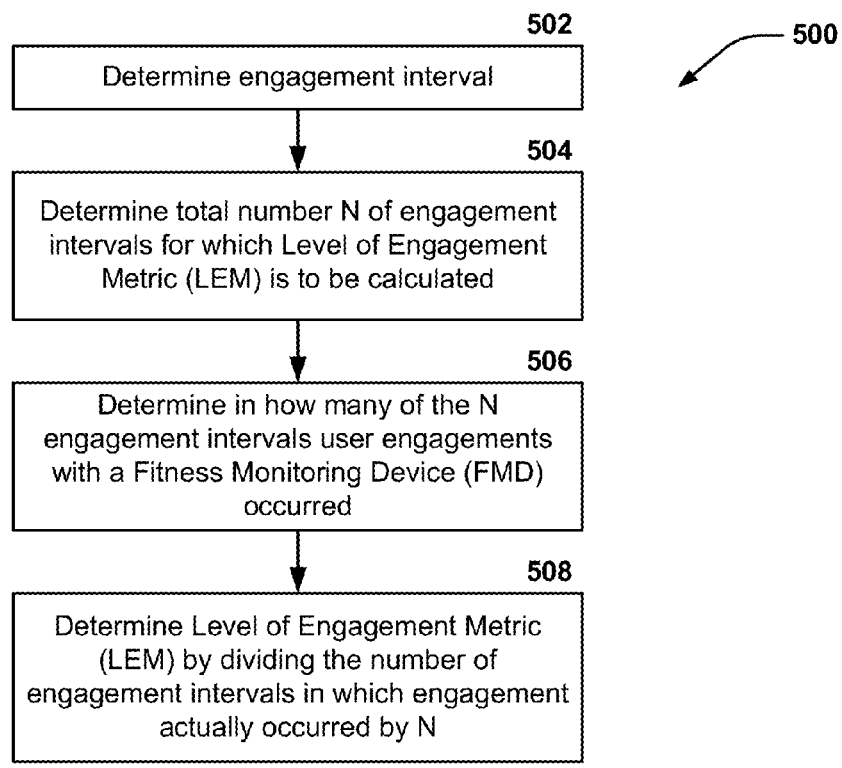
FIG. 5 depicts a flow diagram of one technique for determining a level of engagement metric.

FIG. 5 depicts a flow diagram of one technique for determining a level of engagement metric. In FIG. 5, technique 500 begins in block 502 with the determination of a user engagement interval. The user engagement interval may be the smallest unit of time for which it may be desirable to determine if user engagement with a fitness monitoring device has occurred. For example, in a study conducted by the present inventors and discussed later below, the user engagement interval was a day. The data for each user was then evaluated to determine on how many of those days the user used the body weight scale to obtain a weight measurement. Other user engagement intervals may also be used, e.g., weeks or half-days, depending on which engagement intervals appear to produce level of engagement metrics that are most indicative of a person's actual engagement with a fitness monitoring device.

In block 504, the total number N of engagement intervals (counting backwards from the current engagement interval) for which a level of engagement metric is to be calculated may be determined. In some implementations, the number N may equal the number of engagement intervals that has elapsed since the fitness monitoring device was first activated, i.e., the total lifespan thus far of the fitness monitoring device. For example, if a fitness monitoring product was first activated by a person 421 days ago, for example, by configuring the fitness monitoring product such that data from the fitness monitoring product is associated with that person, then N may be 421 if the engagement interval is 1 day. In other implementations, however, the number N may be set to a value other than the entire lifespan of the fitness monitoring device. For example, N may be 28 and the engagement interval may be 1 day, which would result in level of engagement metric that is based on the last 4 weeks of potential user engagements with the fitness monitoring device.

After determining the total number N of engagement intervals for which the level of engagement metric is to be calculated, the number of those N engagement intervals in which user engagement with the fitness monitoring device actually occurred may be tallied up in block 506. In block 508, the number of the N engagement intervals in which any actual user engagement with the fitness monitoring device occurred may be divided by N. Thus, for example, if a person measured themselves with a body weight scale once a day on 10 days with N=28 days, twice a day on 5 other days of the 28 days, then the level of engagement metric for this example may be (5+10)/28=~54% (in this technique, it does not matter how often a person weighs themselves within a given engagement interval beyond the first weighing).

Figure 6:
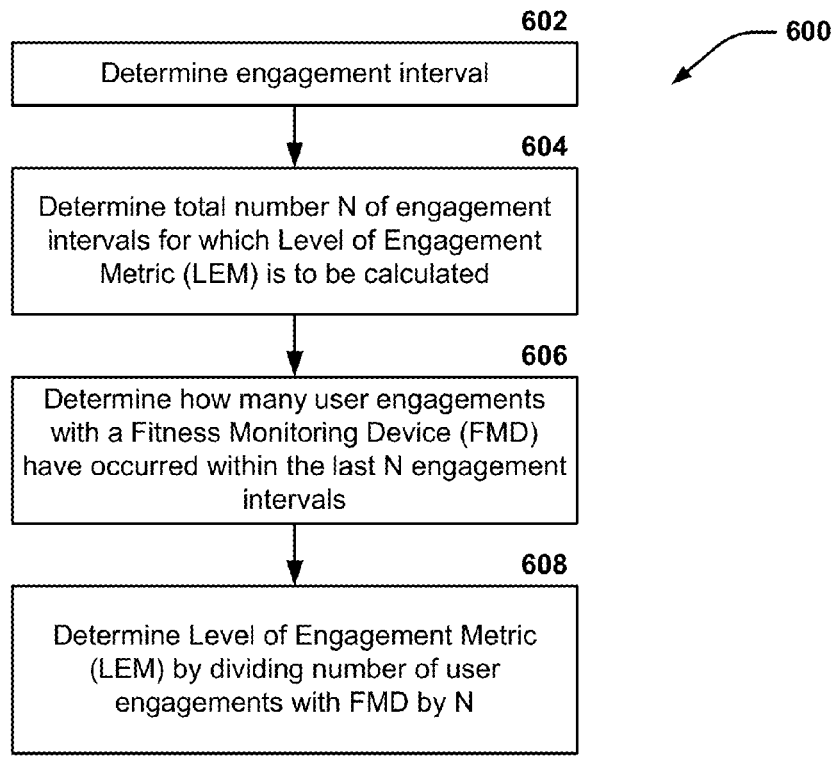
FIG. 6 depicts a flow diagram of another technique for determining a level of engagement metric.

FIG. 6 depicts a flow diagram of another technique for determining a level of engagement metric. In FIG. 6, the technique 600 begins in blocks 602 and 604 with, as in technique 500, the determination of an engagement interval and the number of engagement intervals that will be used to determine the level of engagement metric, respectively. In block 606, however, the technique may differ somewhat from the technique 500 in that the total number of user engagements with the fitness monitoring device over the N engagement intervals may be tallied up and then, in block 608, divided by N. Thus, using the previous example, the total number of user engagements with the fitness monitoring device over the N=28 days period is 10*1+5*2=20, and the level of engagement metric may thus be calculated as being ~71% (in some implementations, the total number of user engagements within the N engagement intervals may not be divided by N at all—N may simply act to limit the number of engagement intervals that are considered). In this scenario, the level of engagement metric may exceed 100% if a person weighs themselves more than N times within the measurement period. In some alternative implementations, the contribution of user engagements beyond the first user engagement with a fitness monitoring device within a given engagement interval to the level of engagement metric may be adjusted, e.g., discounted or capped. For example, each user engagement first with a fitness monitoring device beyond the first in any given engagement interval may be treated as having half as much influence as the first user engagement on the level of engagement metric. In some additional or alternative such implementations, there may be a cap on how many user engagements within a given engagement interval may contribute to the calculation of the level of engagement metric. For example, instances of user engagement with a fitness monitoring device beyond the first, second, and third user engagements within a given engagement interval may simply be ignored when it comes to determining the level of engagement metric. Such capping may be combined with the above-described discounting.

Figure 7:
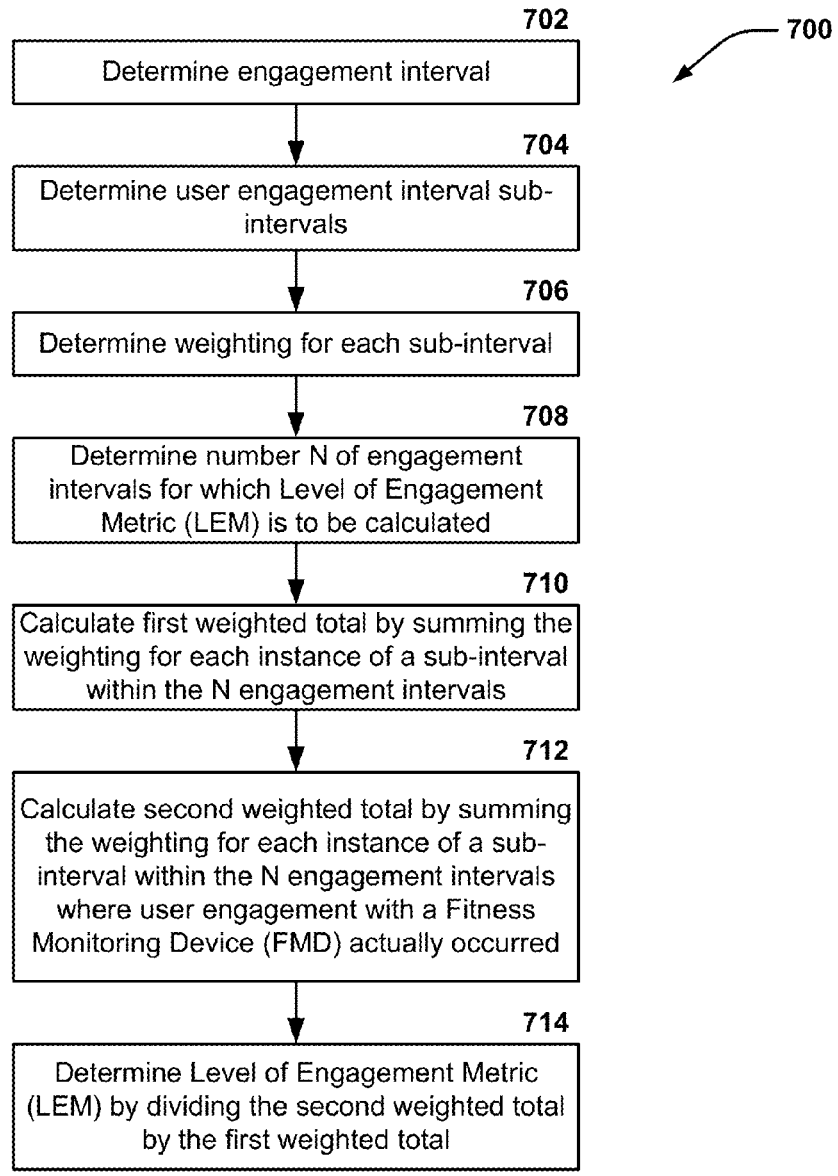
FIG. 7 depicts a flow diagram of a technique for determining a level of engagement metric that utilizes a weighted contribution paradigm.

FIG. 7 depicts a flow diagram of a technique for determining a level of engagement metric that utilizes a weighted contribution paradigm. In FIG. 7, technique 700 begins in block 702 with the determination of a user engagement interval. In block 704, sub-intervals of the engagement intervals may be determined. For example, if the engagement interval is determined to be 1 week, the sub-intervals may be determined to be Monday, Tuesday, Wednesday, Thursday, Friday, Saturday, and Sunday. In block 706, weighting factors for each of the sub-intervals may be determined. For example, the contribution of user engagements with a fitness monitoring device on weekdays may be weighted as having a weighting factor of 1.0, whereas user engagements with the fitness monitoring device on weekends may be weighted as having a weighting factor of 0.5.

In block 708, the number N of engagement intervals for which a level of engagement metric is to be calculated may be determined. The number N may, in some implementations, begin, end, or begin and end with partial engagement intervals, e.g., the engagement interval may be a calendar week spanning from Monday through Sunday, but the first engagement interval may only include Thursday through Sunday, and the final engagement interval may only include Monday through Tuesday. Thus, N may not be a whole number.

In block 710, a first weighted total may be calculated by summing the weighting for each instance of each instance of a sub-interval within the N engagement intervals. For example, if the week-long engagement interval discussed above is used and there are 4 engagement intervals that will be used to calculate the level of engagement metric (assume, for this example, that the engagement intervals are not fractional), then the first weighted total may be calculated as 4 engagement intervals*[(1+1+1+1+1)$_{weekday\ weightings}$+ (0.5+0.5)$_{weekend\ weightings}$]=4*6=24.

In block 712, a similar calculation may be performed for sub-intervals where user engagement occurred in order to determine a second weighted total. For example, in the scenario discussed in the previous paragraph, assume that the person weighed themselves at least once during each sub-interval, with the exception of every Thursday and two of the four Saturdays. In such a scenario, the second weighted total may be calculated as 2 engagement intervals* [(1+1+1+0+1)$_{weekday\ weightings}$+(0+0.5)$_{weekend\ weightings}$]+2 engagement intervals*[(1+1+1+0+1)$_{weekday\ weightings}$+(0.5+ 0.5)$_{weekend\ weightings}$]=2*4.5+2*5=19.

In some implementations, the weighting may be determined based on time periods other than that of the engagement interval. For example, winter months may see a natural decline in active behavior (due to inclement weather) over summer months, and user engagements with a fitness monitoring device such as a body weight scale in winter months may be weighted more strongly than user engagements with the fitness monitoring device during summer months since such user engagements may indicate that the person is still very interested in their body weight during periods of time when they may not be exercising at their normal levels.

In block 714, the level of engagement metric may be determined by dividing the second weighted total by the first weighted total, e.g., 19/24=~79%.

It is to be understood that other weighting systems may be used as well, including weightings that are tied to real-world events, e.g., a sub-interval that happens to correlate with a holiday may have a weighting that is adjusted lower than other sub-intervals that otherwise correspond to non-holidays. In other or additional implementations, weightings may be adjusted for sub-intervals for various reasons, some of which may be specific to a particular user. For example, if a person who uses a fitness monitoring device has a smartphone that may communicate with the fitness monitoring device (or with a server that may be in communication with the fitness monitoring device and that may calculate the level of engagement metric), data from the smartphone, which may have GPS or other location-determination technology, may be used to identify specific sub-intervals where the person may not have been physically able to engage with the fitness monitoring device. For example, if the fitness monitoring device is a body weight scale located in the person's home, GPS data from the person's smartphone (or other device) may indicate that the person was in another city for 4 consecutive sub-intervals, e.g., on a business trip, and may adjust the weightings for those specific sub-intervals such that the failure to engage with the fitness monitoring device during those sub-intervals has a reduced impact on the level of engagement metric. Alternatively, the lack of user engagement in such sub-intervals may simply be ignored in calculating the level of engagement metric (for example, if a 28-day period is evaluated, and it is determined that on days 11-14 of the period, the person was out-of-town and physically unable to engage with a fitness monitoring device, the period may be extended to 32 days and days 11-14 may be ignored).

In some other weighting implementations, data specific to a particular person other than location data (or in conjunction with location data) may be used to adjust weightings for user engagements. For example, if the system that determines level of engagement metrics for the person has access to the person's personal calendar, it may be determined whether or not the person was very busy during a particular sub-interval (based on the degree to which that sub-interval is occupied with scheduled events). If the person is very busy during a given sub-interval, then the weighting for the user engagement for that sub-interval may be adjusted such that a user engagement for that sub-interval has a greater weight (this is appropriate since the person, despite the busy schedule, still took time to use the fitness monitoring device during that sub-interval, demonstrating a higher degree of engagement than might otherwise be expected) than for similar sub-intervals where the person is not very busy.

In some implementations, other information may be factored into a weighting system for determining level of engagement metrics. For example, it may be desirable for a person tracking weight history to take daily measurements of their weight using a fitness monitoring device such as a body weight scale at the same time of day. Accordingly, within each sub-interval, there may be sub-partitions, e.g., a sub-interval with a length corresponding with one day may have 24 one-hour sub-partitions. The weighting for a particular subinterval's user engagement may depend on in which sub-partition(s) of the sub-interval a user engagement occurred. For example, a user engagement with a body weight scale in the 6:00 AM to 8:00 AM sub-partition for a give n subinterval may be weighted higher than a user engagement with the body weight scale that occurs in the 12:00 AM to 6:00 AM and 8:00 AM to 12:00 PM sub-partitions. Thus, the level of engagement metric in this scenario may also incorporate not only the frequency of the user engagement with the fitness monitoring device, but may also incorporate an aspect of data quality (without necessarily referencing the fitness parameters actually measured using the fitness monitoring device).

Other factors that may be used to determine weightings for a given subinterval may include, for example, the weather during a given subinterval, the location where the fitness monitoring device is located, etc.

Figure 8:
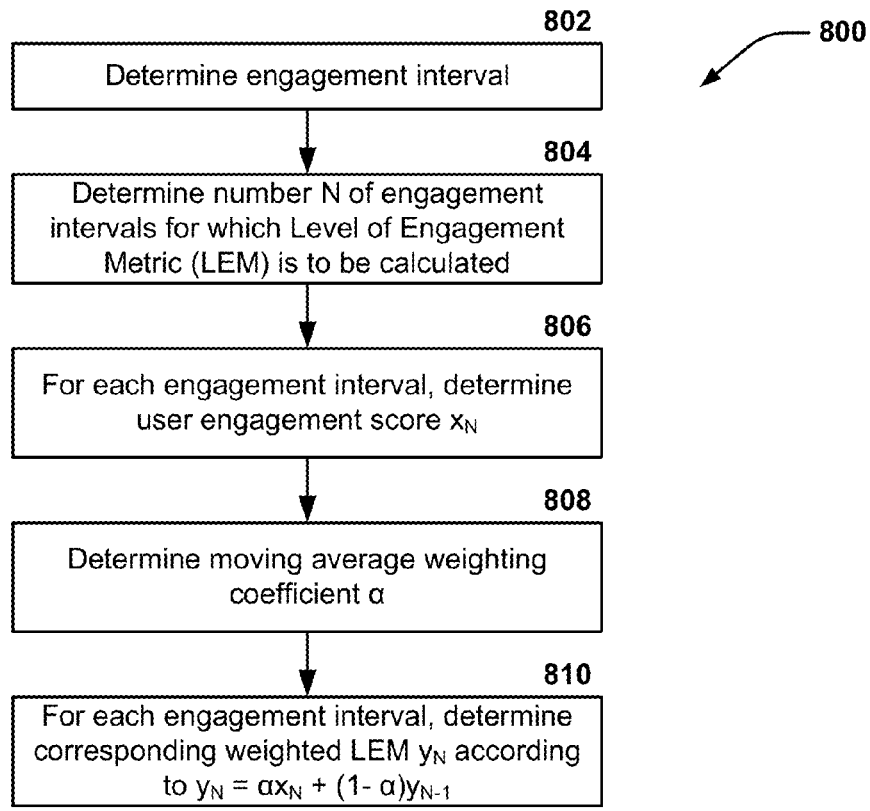
FIG. 8 depicts a flow diagram of another technique for determining a level of engagement metric that utilizes a weighted contribution paradigm.

FIG. 8 depicts a flow diagram of another technique for determining a level of engagement metric that utilizes a weighted contribution paradigm. In FIG. 8, technique 800 begins, as with techniques 500 through 700, with a determination of an engagement interval in block 802. In block 804, the number N of engagement intervals that will be used to determine a level of engagement metric may be determined. In block 806, a user engagement score $x_N$ may be determined (this may, for example, be as simple as a 1 if there was user engagement in the engagement interval and 0 if there was not; in some implementations, the user engagement score may be more nuanced, e.g., indicating the number of user engagements within the engagement interval or other information) for each engagement interval. In block 808, a moving average coefficient $\alpha$ may be determined, where $0 \le \alpha \le 1$; higher values of a may emphasize more recent user engagements over less recent user engagements. The moving average coefficient $\alpha$ may be calculated or determined and then kept fixed for a large number of level of engagement metric determinations. After a moving average coefficient is determined in block 808, a weighted level of engagement metric $y_N$ may be determined according to $y_N = \alpha x_N + (1-\alpha) y_{N-1}$.

In addition to being influenced by the frequency of a person's actual user engagement with a fitness monitoring device, the level of engagement metric may also be determined such that other factors may influence the metric. Such other factors may be separate from the frequency of user engagement, but may nonetheless correlate strongly with the person being "engaged" with the fitness monitoring device. For example, a person's social networking posts, e.g., Twitter posts or Facebook posts, email, text messages, or other communications accessible to a server that determines a level of engagement metric may be used to adjust a level of engagement metric upwards if text analysis of such posts, email, texts, or other communications indicates that the person mentions the fitness monitoring device frequently, or is generally concerned with a fitness parameter that the fitness monitoring device measures. For example, if a person does not engage with a body weight scale fitness monitoring device on a particular day, but mentions the body weight scale or losing weight in an email to a friend on that day, it may indicate that the person is, while not using the body weight scale that day, at least thinking about it or about a fitness parameter that it measures.

Another factor that may be used to adjust a level of engagement metric (in addition to frequency of user engagement) is whether or not the person owns/uses another fitness monitoring device. For example, a person who owns a wearable activity tracker in addition to using a body weight scale may be viewed as being more engaged with the body weight scale (or with their health in general). Other factors that may cause an upwards adjustment in a persons' level of engagement metric may include obtaining a gym membership, enrolling in a fitness program, playing fitness-oriented games on video consoles, enrolling in fitness-related events such as 5K walks or races, frequent logging of foods consumed and types of food consumed, e.g., via Fitbit's website, the activity levels of friends of the person, etc.

The level of engagement metric for a person may be further adjusted based on, for example, demographic characteristics of the person, e.g., age group, gender, lifestyle (sedentary v. highly-active, physical tradesperson v. office worker, etc.), etc., that allow various people in the sample set to be clustered into groups. If certain groups exhibit certain tendencies, e.g., some groups may never be home on weekends, the level of engagement metric may be adjusted to ignore or place very little weight on certain intervals, e.g., subintervals falling on a weekend.

It is to be understood that the techniques discussed herein may also, in some implementations, be practiced without the specific temporal demarcations used herein, i.e., "engagement intervals" and/or "sub-intervals." For example, instead of engagement intervals with weighted sub-intervals, each engagement interval may be individually weighted (in this example, no sub-intervals may be needed). In the case of "lifetime" level of engagement metrics, there may be only one engagement interval that is coextensive with the current lifespan of the fitness monitoring device (or at least of the person's association with the fitness monitoring device).

In variant of the technique of FIG. 5, the present inventors performed a post-hoc analysis on 10,000 users of the Fitbit Aria™, a consumer Wi-Fi scale released in May of 2012 that automatically identifies a user from a pool users who may share the same body weight scale based on their weight and then uploads their weight to a cloud-based storage system. Users were subsampled to ensure an equal fraction of males and females. The median age in the sample was 40 years old, and the 1st, 2nd, and 3rd quartiles of baseline weight were (177, 200, 229 lbs) and (134, 154, 185 lbs) for males and females, respectively. 6,742 of the sample users also owned a Fitbit accelerometer-based activity tracker, e.g., a Fitbit Ultra™, Classic™, Zip™, One™, or Flex™. The present inventors also statistically corrected for seasonal variation in user weight by sampling an equal number of users with start dates in each month of the year. Weight loss was examined on an absolute and relative basis and compared against user engagement with the Aria™ scale as indicated by the frequency with which each user utilized the scale and the ownership and/or use (or lack thereof) of an activity tracker.

The present inventors discovered that users lost an average of 3.00±0.19 lb (1.46±0.09%) in the first 60 days of usage. Subjects that weighed themselves daily lost an average of 6.69±1.03 lb (3.26±0.48%). In contrast, subjects that weighed themselves once a week lost 1.44±0.35 lb (0.64±0.16%). The present inventors also determined that users that used a Fitbit activity tracker in addition to the Aria scale lost more weight than users that just used a scale (3.51±0.25 lb versus 2.61±0.29 lb, p<0.00077).

The present inventors have discovered that the facultative use of voluntary, unprompted, consumer weight scales, accounting for seasonal variation, leads to significant weight loss on the order of 3.00 lb over 60 days of usage. The present inventors have also determined that frequent voluntary weighing, as opposed to frequent weighing at the behest of a third party, is highly correlated with weight loss, with daily weighers losing roughly 4.5 times more than weekly weighers. Furthermore, the present inventors have also discovered that, as a secondary effect, the usage of an activity tracker in addition to a body weight scale correlated to more weight loss than for subjects who did not use one.

The level of engagement metric may also be used to present a statistical measure of the impact of a particular notification on the level of engagement metric for a person (or on fitness parameters associated with the person).

For example, using data from a population of users, the process may calculate a standard score such as a z-score, which shows whether some aspect of the user's fitness (or level of engagement metric) has improved in a statistically significant manner.

These statistical measures may represent how the user has changed his or her behavior in response to using or owning the biometric monitoring device. In one example, the metric is based on a statistical hypothesis test such as z-test and/or t-test applied to a weight measurement and/or weight changing trend before and after owning an activity tracker. The tests can be applied on the weight measurements and/or weight changing trend before and after the user interacts via various user interactions methods.

For example, a level of engagement metric for a person over two 30-day windows bracketing the use of a particular type of notification may be evaluated. The first set may consist of 30 user engagement samples from 30 days before the notification, and the second set may consist of 30 user engagement samples from 30 days after the notification. A two sample z-test (or t-test) may be performed to see if the two sample groups are drawn from different distributions, formally, first group $\sim N(\mu_1, \Sigma)$ and second group $\sim N(\mu_2, \Sigma)$, with the null hypothesis as $\mu_1 = \mu_2$, and alternative is $\mu_1 != \mu_2$.

If the statistical test fails to reject the null, this may be interpreted as indicating that the notification was ineffective in producing a change in user engagement. If the statistical test succeeds and rejects the null, then that may be interpreted as indicating that the notification was effective in causing the person to change their engagement level—such a technique may be used to determine which types of notifications are most effective at influencing a particular person's behavior.

Such an approach may also be used with other data types, e.g., fitness parameter data such as steps taken per day, stairs climbed, etc., and may also be applied to other data such as calorie intake before/after a notification.

As discussed previously, based on a level of engagement metric determined using any of the techniques described herein, a determination may be made as to whether or not to generate a notification designed to encourage user engagement with the fitness monitoring device. Such a determination may be based on the level of engagement metric indicating, for example, that a person's level of engagement metric over the last month was lower than a predetermined or calculated ideal, e.g., the average level of engagement metric for other people with lower average weight than the person or that may, on average, have lost more weight than the person within the same time period.

In addition to the various techniques discussed in detail above for determining a level of engagement metric for a person, several techniques for encouraging increased user engagement are discussed in detail below. Encouraging increased user engagement may be warranted when the level of engagement metric falls below a certain level for a person, e.g., indicating less than 1 user engagement per day on average over the previous month.

Figure 9:
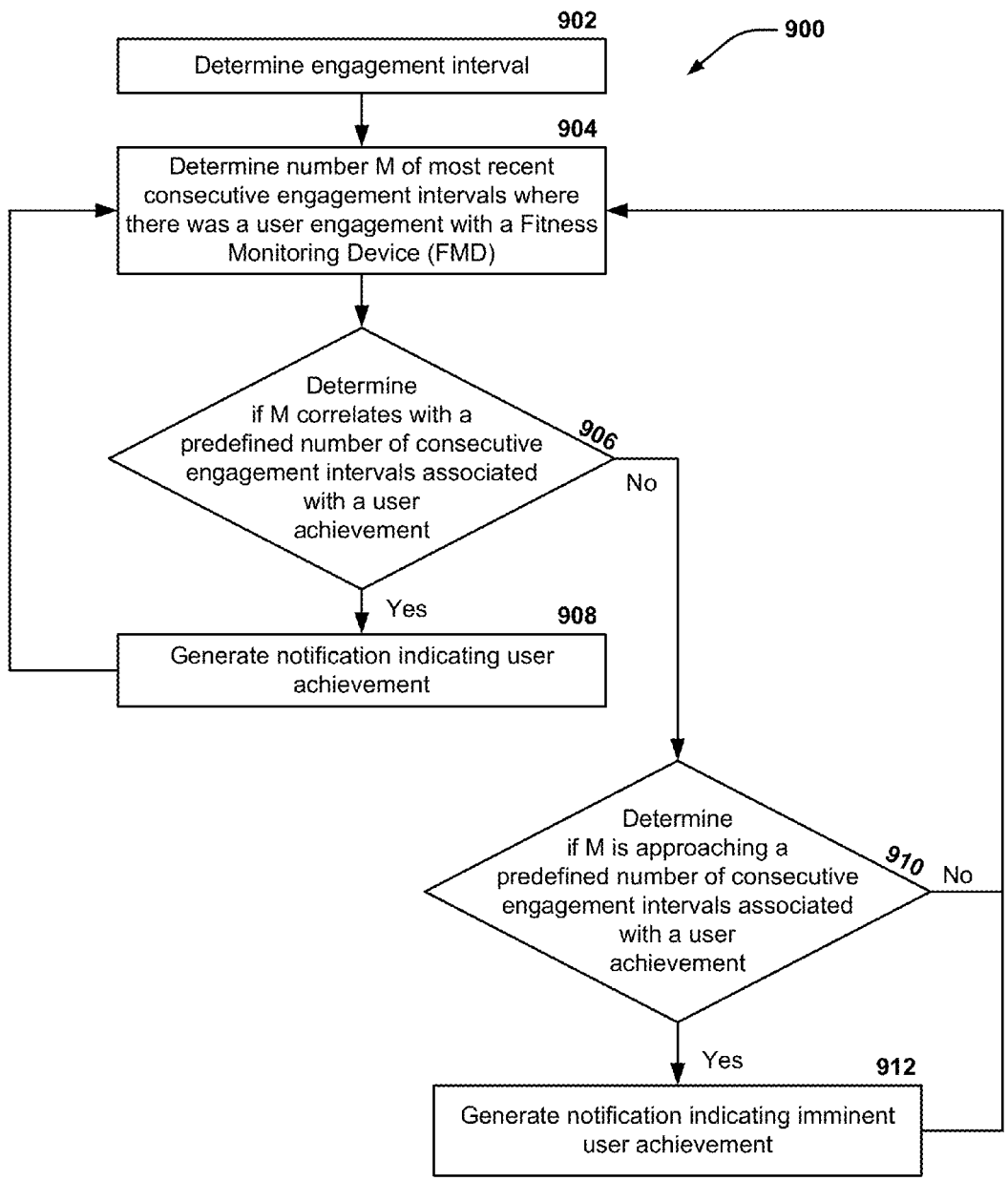
FIG. 9 depicts a flow diagram of a technique for encouraging increased user engagement with a fitness monitoring device.

FIG. 9 depicts a flow diagram of a technique for encouraging increased user engagement with a fitness monitoring device. In FIG. 9, technique 900 starts in block 902 with the determination of an engagement interval, e.g., a day, a week, etc. In block 904, the number M of the most recent consecutive engagement intervals in which there was actually user engagement with a fitness monitoring device may be determined. For example, if a person used the fitness monitoring device at least once a day for the last five days (but not on the sixth day), then M=5.

In block 906, a determination may be made as to whether or not M correlates with a predefined number of consecutive engagement intervals associated with a particular user achievement, e.g., a "1 week of streak" badge that indicates that the person weighed themselves on a body weight scale every day for a week (7 days). If the determination in block 906 is that M correlates with the predefined number of consecutive engagement intervals, then the technique may continue to block 908, where a message or other communication indicating the user achievement may be generated; the message or other communication indicating the achievement may serve as a notification, as discussed previously. After block 908 is complete, the technique may return to block 904 (after performing any re-sets to avoid a multiple-award scenario in which the user obtains multiple achievements/badges).

If it is determined in block 906 that M does not correspond with the predefined number of consecutive engagement intervals associated with the particular user achievement, the technique may proceed to block 910, where a further determination may be made as to whether or not M is approaching, i.e., in close proximity to, a predefined number of consecutive engagement intervals. For example, if M=5 and the predefined number of consecutive engagement intervals is 7, then M may be within two units of the predefined number (which may be, in this example, in close proximity to the predefined number), and the technique may proceed to block 912, where a notification may be generated that includes information that may indicate that the person is getting close to the achievement, e.g., a message stating "You've weighed yourself 5 days in a row! Great job! Only two more days to go before you get the '1 Week Streak' badge! Don't slack off!" After block 912, the technique may return to block 904 (as it may if M is not determined to be approaching the predefined number of consecutive engagement intervals).

Figure 10:
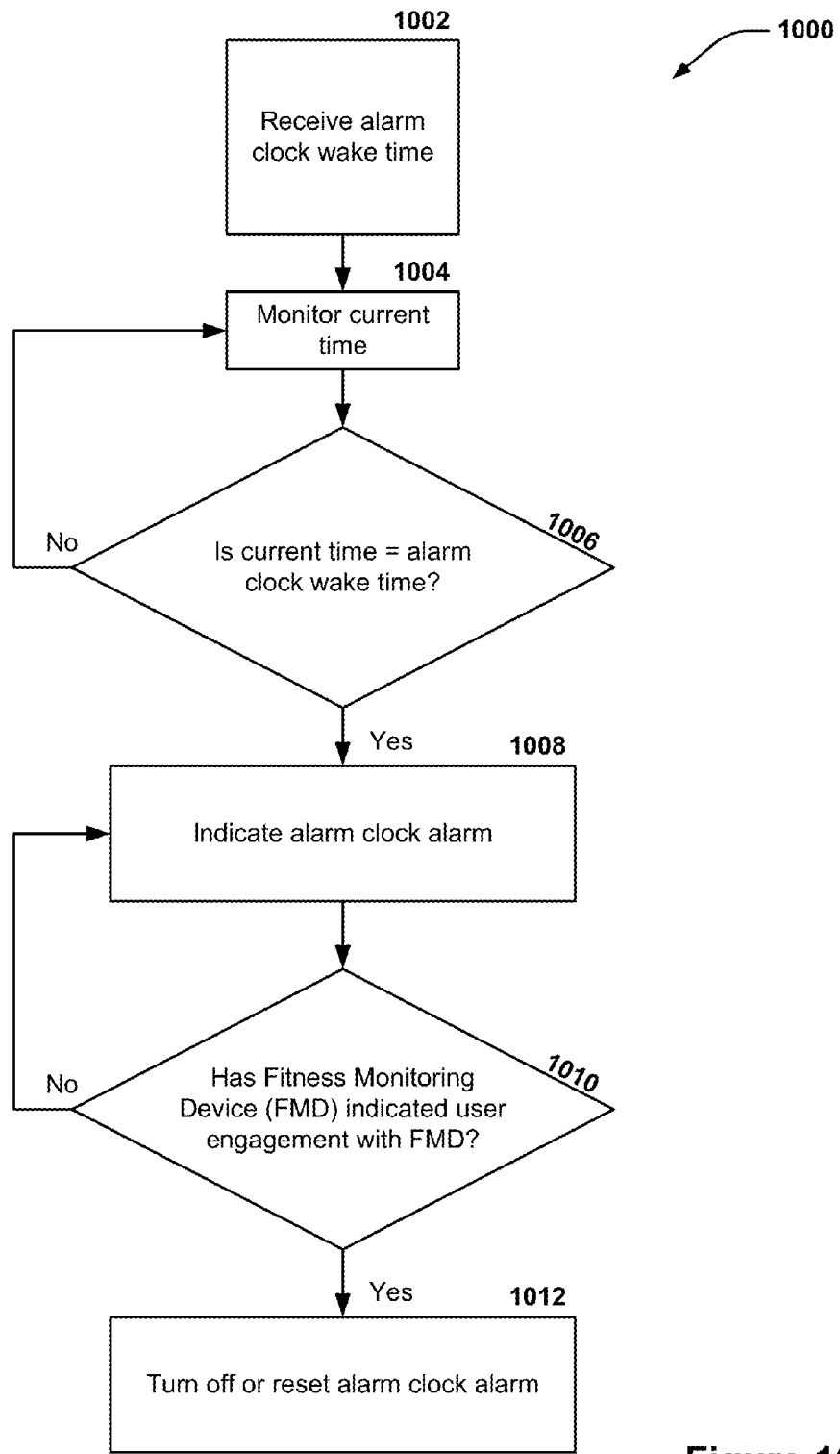
FIG. 10 depicts a flow diagram of a technique for encouraging increased user engagement with a fitness monitoring device that involves combining the fitness monitoring device with alarm clock functionality.

FIG. 10 depicts a flow diagram of a technique for encouraging increased user engagement with a fitness monitoring device that involves combining the fitness monitoring device with alarm clock functionality.

In FIG. 10, technique 1000 begins in block 1002 with the receipt of an alarm clock wake time. The technique may continue in block 1004, where the current time may be obtained. After obtaining the current time, the technique may continue to block 1006 where a determination may be made as to whether or not the current time equals the alarm clock wake time. If it is determined in block 1006 that the current time does not equal the alarm clock wake time, then the technique may return to block 1004. If it is determined in block 1006 that the current time equals the alarm clock wake time, then the technique may continue to block 1008, where an alarm clock alarm may be indicated, e.g., through the use of a buzzer, vibramotor, chime, lights, etc. The alarm may be emitted by a fitness monitoring device, or by another device, e.g., a stand-alone alarm clock or by a smartphone having an appropriate app loaded. The technique may proceed to block 1010, where a determination may be made as to whether or not a fitness monitoring device has indicated user engagement after the triggering of the alarm. If block 1010 determines that the person has engaged with the fitness monitoring device, then the technique may proceed to block 1012, where the alarm may be turned off. If block 1010 determines that the person has not engaged with the fitness monitoring device, then the technique may return to block 1008 and continue to indicate the wake alarm.

In some implementations, the technique 1000 may take into account a level of engagement metric in order to determine if the person must engage with the fitness monitoring device, e.g., a body weight scale, in order to shut off the alarm. For example, an app on a smartphone may provide the alarm clock functionality. The app may, when the alarm goes off, query a server (or other resource) to determine if the level of engagement metric associated with a person, e.g., the owner of the smartphone, is at or above a desired level. If so, then the smartphone app may allow the person to turn off the alarm without engaging with the fitness monitoring device. If not, then the smartphone app may be configured such that it will not turn off until it receives a confirmation from the fitness monitoring device, either directly or via an intermediary such as a server, that the person has engaged with the fitness monitoring device.

Figure 11:
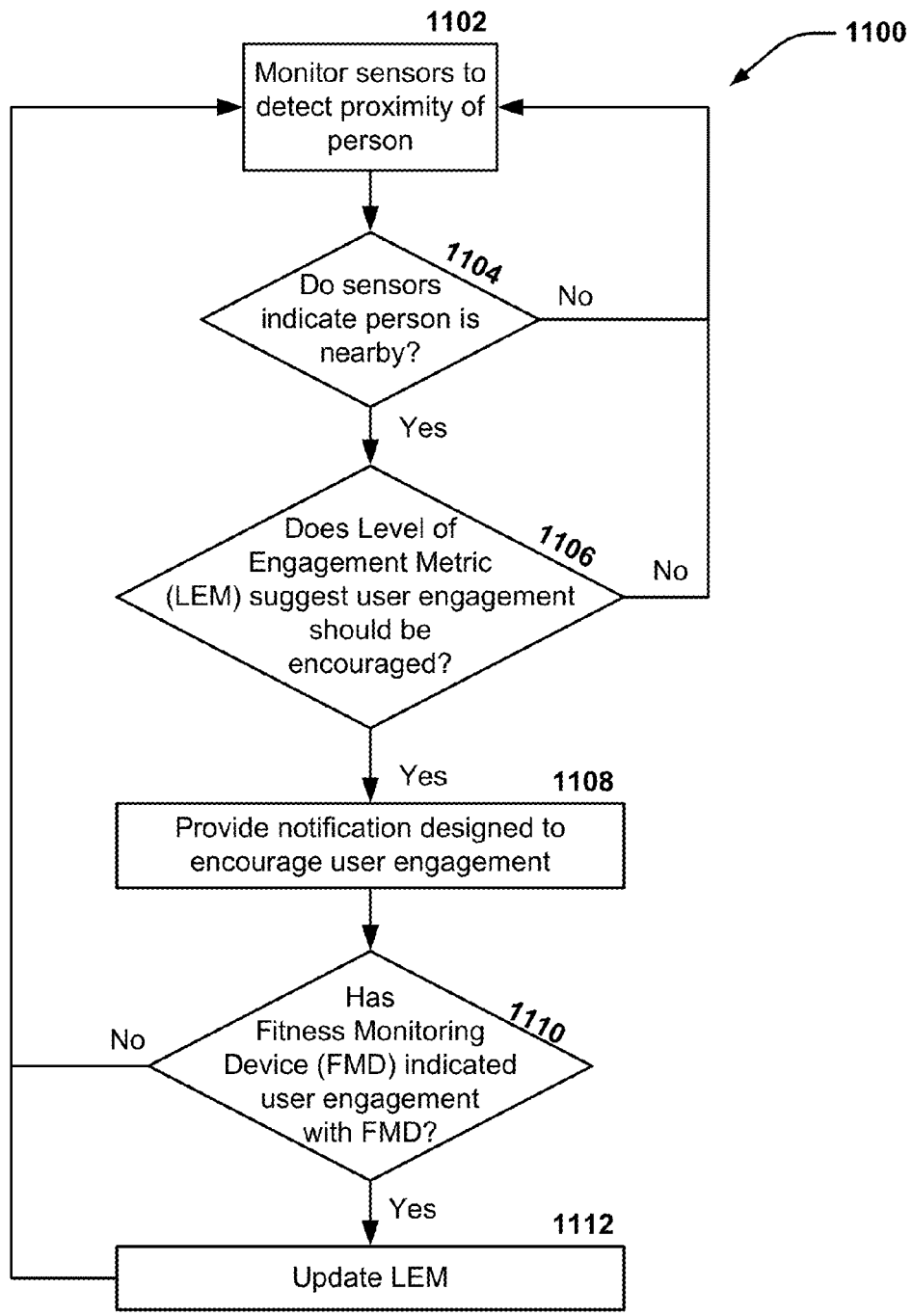
FIG. 11 depicts a flow diagram of a technique for encouraging increased user engagement with a fitness monitoring device that has a proximity detection system.

FIG. 11 depicts a flow diagram of a technique for encouraging increased user engagement with a fitness monitoring device that involves combining the fitness monitoring device with a proximity detection system.

In FIG. 11, technique 1100 begins in block 1102, where one or more sensors that may detect the proximity of a person to a fitness monitoring device, e.g., a body weight scale, may be monitored. The one or more sensors may be located in the fitness monitoring device and may, for example, include motion sensors configured to detect the person's movement, microphones configured to detect sounds such as footsteps or speech, cameras configured to detect visual or IR signatures of the person, $CO_2$ sensors or particle counters configured to detect exhalations of a person, RF sensors configured to detect the signal strength of a smartphone or another fitness monitoring device worn by the person, etc.

In block 1104, a determination may be made as to whether the sensors indicate that the person is nearby. Such a determination may be made through any of a variety of measures, including facial recognition via camera, identification of a paired electronic device such as a smartphone that is close enough that the fitness monitoring device can determine from the signal received from the paired electronic device the identity of the person (and their approximate range by the signal strength of that signal), etc. If it is not determined in block 1104 that the person is nearby, the technique may return to block 1102. Otherwise, the technique may continue to block 1106, where a further determination may be made as to whether or not the person is associated with a level of engagement metric that indicates that the user should be encouraged to engage with the fitness monitoring device. In some implementations, this may be based on a level of engagement metric that indicates whether or not the person has engaged with the fitness monitoring device at all during the present engagement interval (in implementations where the sensor can determine proximity but not identity, e.g., when a microphone is used to detect footsteps, this determination may be more general, e.g., has any person associated with the fitness monitoring device not yet engaged with the fitness monitoring device).

If it is determined in block 1106 that encouraging user engagement is unnecessary, the technique may return to block 1102. If, however, it is determined in block 1106 that encouraging user engagement is necessary or recommended, then a notification may be generated in block 1108 that is designed to encourage user engagement by the person. For example, the fitness monitoring device may start flashing a super-bright LED, emit a melody, or otherwise draw attention to itself.

After generating the notification in block 1108, the technique may proceed to block 1110, where a determination may be made as to whether the fitness monitoring device has indicated that user engagement has occurred. If not, then the technique may return to block 1102 (allowing the notification to be turned off if the person is no longer nearby). If so, then the technique may proceed to block 1112, where the level of engagement metric may be updated to reflect that user engagement has occurred. The technique may then return to block 1102. In this manner, the fitness monitoring device may actively monitor for nearby potential users and, if conditions, e.g., the level of engagement metric, warrant, attempt to attract the potential user's attention and provoke a user engagement with the fitness monitoring device.

Figure 12:
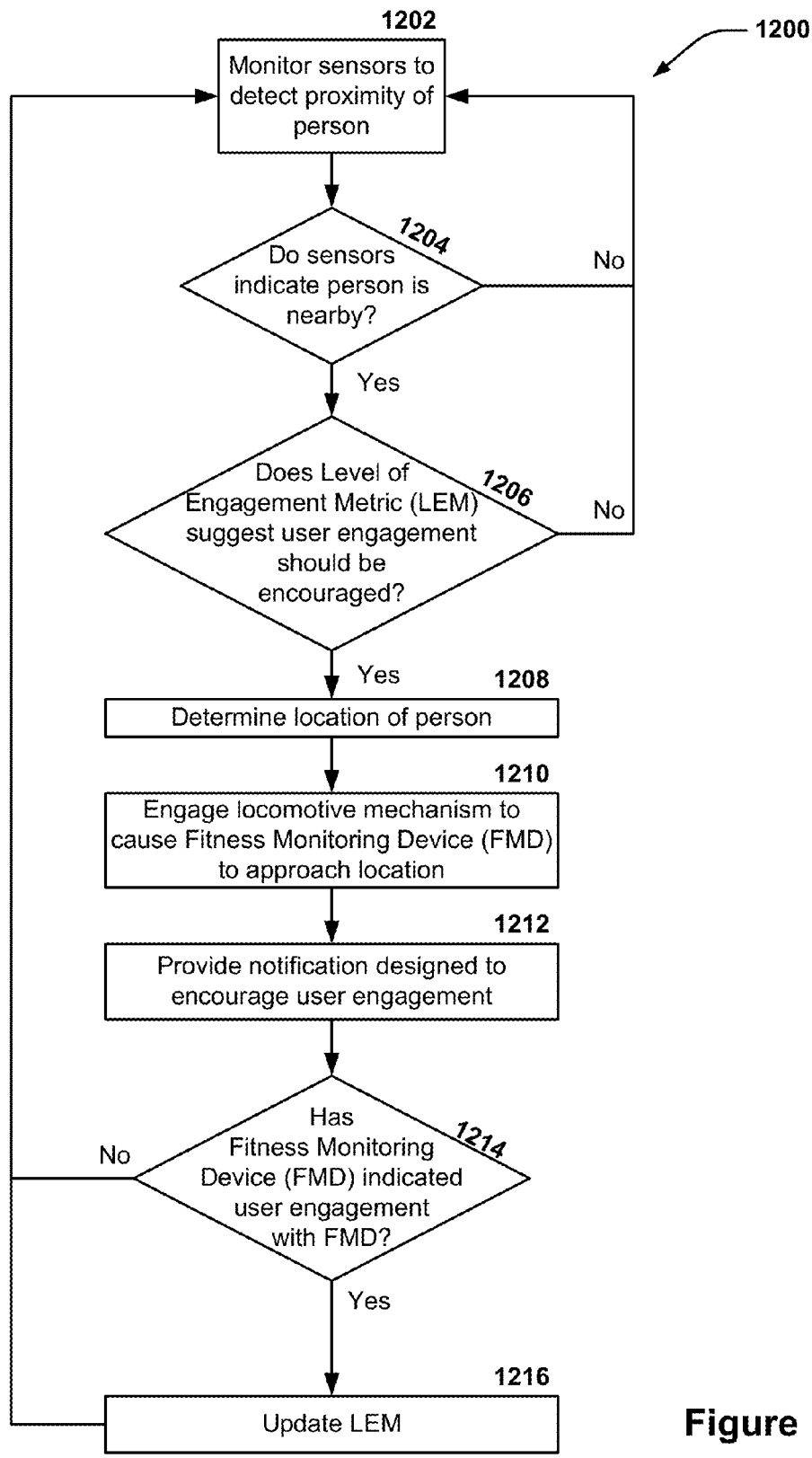
FIG. 12 depicts a flow diagram of a technique for encouraging increased user engagement with a fitness monitoring device that involves combining the fitness monitoring device with a proximity detection system and a locomotive mechanism.

FIG. 12 depicts a flow diagram of a technique for encouraging increased user engagement with a fitness monitoring device that involves combining the fitness monitoring device with a proximity detection system and a locomotive mechanism.

In FIG. 12, technique 1200 may begin in a similar manner to technique 1100, i.e., blocks 1202, 1204, and 1206 may generally correspond to the steps taken in blocks 1102, 1104, and 1106. If it is determined in block 1206 that the level of engagement metric indicates that user engagement should be encouraged, the technique may proceed to block 1208, where the location of (or heading pointing towards) the person detected in block 1204 may be determined. After determining the location of the person in block 1208, the technique may proceed to block 1210, where the fitness monitoring device may be caused to move towards the person. For example, the fitness monitoring device may be equipped with wheels, treads, or other locomotive mechanism allowing it to move across the floor and navigate a room. The fitness monitoring device may be configured to perform rudimentary movement, e.g., a single, straight-line movement towards a person, or may be configured to be more aggressive, e.g., following the person around the room. In some implementations, the fitness monitoring device may move away from the person, or in some other direction. For example, if a fitness monitoring device that has a locomotive mechanism as described above, such as a body weight scale, is combined with a fitness monitoring device that has an alarm clock functionality (as also described above), it may be desirable to have the fitness monitoring device not only provide the alarm functionality but also move away from the person at the same time, forcing the person to walk to the fitness monitoring device in order to weigh themselves and thereby turn off the alarm.

The technique may then proceed to block 1212, in which a notification may be generated. In some implementations, the movement of the fitness monitoring device may serve as the notification (for example, the mere fact that a body weight scale is following a person around a room may serve as a reminder and/or encouragement for the person to weigh themselves). In other implementations, in addition to movement, the fitness monitoring device may also utilize other mechanisms for notifying the person that they should weigh themselves, e.g., light, sound, etc.

In block 1214, a determination may be made as to whether the fitness monitoring device has indicated that user engagement has occurred. If not, then the technique may return to block 1202. If so, then the technique may proceed to block 1216, where the level of engagement metric may be updated to reflect that user engagement has occurred. The technique may then return to block 1202. In this manner, the fitness monitoring device may actively monitor for nearby potential users and, if conditions, e.g., the level of engagement metric, warrant, attempt to attract the potential user's attention and provoke a user engagement with the fitness monitoring device.

It is to be understood that aspects of the techniques described herein, e.g., the calculations used to determine the level of engagement metric, the determination of whether to generate a notification (and what form that notification should take, etc.), may be adjusted over time via a learning algorithm (e.g., neural network). Neural networks are particularly adept at learning and improving interactions with users (whether by notifications or otherwise). Connections between nodes within the network are strengthened or weakened based on inputs received over time. Interactions that improve a user's health or increase the user's level of engagement may be recommended more strongly as the neural network gains experience.

For example, the data collected may show that a specific notification and/or notification mechanism, e.g., flashing LEDs on the fitness monitoring device, has a stronger effect on changing a specific person's behavior; the techniques may then adjust to emphasize notifications provided in this way.

Devices implementing the techniques discussed herein may also use information and data from other users, internet sources, academic papers, etc. to learn how to function and adapt their behavior. Thus, such devices will be able to learn from the individual user, from every other user using similar devices, and also from the larger body of information available via the internet. For example, such devices may learn what intervention patterns have worked for similar users in the past or in clinical studies, and use this information to determine how to interact with a new user.

In some implementations, the fitness monitoring device may learn to use different interactions (e.g., tones of voice) based on the time of day, the day of week, and the season. Additionally, the fitness monitoring device may learn the preferred language, dialect, or accent of the user to better communicate with them.

In another implementation, the fitness monitoring device may learn how to best serve a specific user based on their normal schedule or changes in their schedule. For example, a scheduled party may lead to the device interacting with the user with a reminder to go to the party or increase their activity to offset calories consumed at the party.

In another implementation the fitness monitoring device may use the user's historical data in conjunction with other users' behavior to determine correlations between certain activities and outcomes. For example, increased activity, longer sleep duration, or increased weigh frequency may lead to increased weight loss. The fitness monitoring device may learn how to report these findings to the user in a way that maximizes a specific goal (e.g., maximum clarity, or ease of understanding).

In some other implementations, the fitness monitoring device may learn what types of user interaction the user prefers. For example, the fitness monitoring device may determine the preferred goal celebration (e.g., badge, social media post, voice message), and then use this information to maximally incentivize certain goals. For instance, the preferred goal celebration may be reserved for milestone goal achievements.

Unless the context of this disclosure clearly requires otherwise, throughout the description and the claims, the words "comprise," "comprising," and the like are to be construed in an inclusive sense as opposed to an exclusive or exhaustive sense; that is to say, in a sense of "including, but not limited to." Words using the singular or plural number also generally include the plural or singular number respectively. Additionally, the words "herein," "hereunder," "above," "below," and words of similar import refer to this application as a whole and not to any particular portions of this application. When the word "or" is used in reference to a list of two or more items, that word covers all of the following interpretations of the word: any of the items in the list, all of the items in the list, and any combination of the items in the list. The term "implementation" refers to implementations of techniques and methods described herein, as well as to physical objects that embody the structures and/or incorporate the techniques and/or methods described herein.

It is to be understood that the use of ordinal indicators, e.g., a), b), c) . . . or the like, does not inherently convey any particular order of operations, but is merely used as a convenient mechanism for referencing different operations or steps of a technique.

There are many concepts and implementations described and illustrated herein. While certain features, attributes and advantages of the implementations discussed herein have been described and illustrated, it should be understood that many others, as well as different and/or similar implementations, features, attributes and advantages of the present inventions, are apparent from the description and illustrations. As such, the above implementations are merely exemplary. They are not intended to be exhaustive or to limit the disclosure to the precise forms, techniques, materials and/or configurations disclosed. Many modifications and variations are possible in light of this disclosure. It is to be understood that other implementations may be utilized and operational changes may be made without departing from the scope of the present disclosure. As such, the scope of the disclosure is not limited solely to the description above because the description of the above implementations has been presented for the purposes of illustration and description.

Importantly, the present disclosure is neither limited to any single aspect nor implementation, nor to any single combination and/or permutation of such aspects and/or implementations. Moreover, each of the aspects of the present disclosure, and/or implementations thereof, may be employed alone or in combination with one or more of the other aspects and/or implementations thereof. For the sake of brevity, many of those permutations and combinations will not be discussed and/or illustrated separately herein.

What is claimed is:

1. An apparatus comprising:
   a housing;
   at least one biometric sensor configured to measure at least one fitness parameter of a person associated with the apparatus;
   a notification mechanism, wherein the notification mechanism is selected from the group consisting of: a visual indicator, a tactile indicator, an audio indicator, an electronic communications interface, and combinations thereof; and
   a controller including one or more processors and a memory, wherein:
      the one or more processors and the memory are communicatively connected, and
      the memory stores instructions that, when executed by the one or more processors, cause the one or more processors to:
         receive an instruction to activate the notification mechanism to indicate that the person associated with the apparatus should use the apparatus to obtain a measurement of the at least one fitness parameter using the at least one biometric sensor, wherein the instruction to activate the notification mechanism is generated, at least in part, in response to a level of engagement metric for the apparatus, wherein the level of engagement metric is determined, at least in part, based on in how many time intervals of a plurality of time intervals within a defined time period the person associated with the apparatus engaged with the apparatus to obtain a measurement of the at least one fitness parameter using the apparatus, and
         cause the notification mechanism to provide an indication that the person associated with the apparatus should use the apparatus to obtain the measurement of the at least one fitness parameter using the at least one biometric sensor.

2. The apparatus of claim 1, wherein the apparatus is a scale and the at least one biometric sensor includes a weight-sensing sensor.

3. The apparatus of claim 1, wherein the indication is provided by an action selected from the group consisting of: activating the visual indicator on the apparatus, emitting an audible sound, emitting an audible melody, emitting a spoken message, vibrating all or part of the apparatus, causing the apparatus to move, sending a wireless signal to a remote device, and combinations thereof.

4. The apparatus of claim 1, further comprising a sensor configured to detect when the person is near the apparatus, wherein the memory stores further instructions for further controlling the one or more processors to:
   cause the notification mechanism to provide the indication that the person should use the apparatus to obtain the measurement of the at least one fitness parameter using the at least one biometric sensor when the sensor indicates that the person is near the apparatus.

5. The apparatus of claim 4, wherein the sensor is selected from the group consisting of a microphone, an accelerometer, a camera, a motion sensor, a $CO_2$ sensor, and a particle counter.

6. The apparatus of claim 4, wherein the sensor is a wireless receiver and is configured to determine that the person is near the apparatus by, at least in part, receiving a wireless signal from a device worn or carried by the person.

7. The apparatus of claim 4, wherein:
   the apparatus is a scale and the at least one biometric sensor includes a weight-sensing sensor, the apparatus further comprising:
      a locomotive drive mechanism configured to move the apparatus across a floor; wherein the memory stores further instructions for further controlling the one or more processors to control the locomotive drive mechanism to move the apparatus in a direction selected from the group consisting of: towards the person and away from the person.

8. The apparatus of claim 7, wherein the memory stores further instructions for further controlling the one or more processors to:
   control the notification mechanism to emit an audible sound or a pre-recorded or synthesized voice message encouraging the person to weigh themselves using the apparatus.

9. The apparatus of claim 7, wherein the apparatus is configured to navigate about a room.

10. The apparatus of claim 1, wherein the memory stores further instructions for further controlling the one or more processors to:
    determine a current time of day;
    determine that the current time of day correlates with a pre-set alarm time; and
    provide the indication via the notification mechanism responsive to the determination that the current time of day correlates with the pre-set alarm time.

11. The apparatus of claim 10, wherein the memory stores further instructions for further controlling the one or more processors to cancel the indication in response to the person associated with the apparatus using the apparatus to obtain the measurement of the at least one fitness parameter using the at least one biometric sensor.

12. The apparatus of claim 11, wherein the indication is a wireless signal sent by the apparatus to a remote device and the instructions for controlling the one or more processors to cancel the indication cause the apparatus to send a second wireless signal to the remote device indicating that the indication is to be canceled.

\* \* \* \* \*